US012788827B2

(12) United States Patent
Mieszawska et al.

(10) Patent No.: US 12,788,827 B2
(45) Date of Patent: Nov. 10, 2026

(54) METHOD OF FORMING PEPTIDE-COATED NANOPARTICLES

(71) Applicants: Research Foundation of the City University of New York, New York, NY (US); Icahn School of Medicine at Mount Sinai, New York, NY (US)

(72) Inventors: Aneta J. Mieszawska, Long Island City, NY (US); Sylwia Dragulska, Brooklyn, NY (US); Mina Poursharifi, Brooklyn, NY (US); Marek Wlodarczyk, Brooklyn, NY (US); Ying Chen, Chappaqua, NY (US); John A. Martignetti, Chappaqua, NY (US); Maxier Acosta Santiago, Brooklyn, NY (US)

(73) Assignees: Research Foundation of the City University of New York, New York, NY (US); Icahn School of Medicine at Mount Sinai, New York, NY (US)

( * ) Notice: Subject to any disclaimer, the term of this patent is extended or adjusted under 35 U.S.C. 154(b) by 165 days.

(21) Appl. No.: 18/506,664

(22) Filed: Nov. 10, 2023

(65) Prior Publication Data

US 2024/0156982 A1 May 16, 2024

Related U.S. Application Data

(60) Provisional application No. 63/383,143, filed on Nov. 10, 2022.

(51) Int. Cl.

| | |
|---|---|
| ***A61K 9/51*** | (2006.01) |
| ***A61K 38/08*** | (2019.01) |
| ***A61K 47/69*** | (2017.01) |
| ***C07K 7/06*** | (2006.01) |
| *B82Y 5/00* | (2011.01) |

(52) U.S. Cl.

CPC ........ *A61K 47/6937* (2017.08); *A61K 9/5169* (2013.01); *A61K 9/5192* (2013.01); *C07K 7/06* (2013.01); *B82Y 5/00* (2013.01)

(58) Field of Classification Search

None

See application file for complete search history.

(56) References Cited

PUBLICATIONS

Chong et al.; "Advances in fabricating double-emulsion droplets and their biomedical applications," 2015, Springer; Microfluid Nanofluid, vol. 19, pp. 1071-1090. (Year: 2015).*

Poursharifi; "Synthesis, characterization and applications of peptide-coated nanoparticles," Dissertation, The City University of New York, Sep. 2021, 137-pages. (Year: 2021).*

Cui et al.; "Dual-Target Peptide-Modified Erthyrocyte Membrane-Enveloped PLGA Nanoparticles for the Treatment of Glioma," 2020 , Frontiers in Oncology, vol. 10, Article 563938, pp. 1-15. (Year: 2020).*

Prakobvaitayakit et al.; "Optimization of Polylactic-Co-Glycolic Acid Nanoparticles Containing Itra-conazole Using 23 Factorial Design," 2003; AAPS, PharmSciTech, vol. 4, No. 4, Article 71, pp. 1-9. (Year: 2003).*

Zhang et al.; "PLGA Nanoparticle-Peptide Conjugate Effectively Targets Intercellular Cell-Adhesion Molecule-1," 2007, ACS; Bioconjugate Chem., vol. 19, pp. 145-152. (Year: 2007).*

Contel, Maria; Organometallic Chemistry and Medicinal Chemistry; Brooklyn College website, Jan. 21, 2021, 10-pages.

Mieszawska, Antea; Brooklyn College website; Sep. 2020, 4-pages.

Dragulaska, S. et al.; Engineering and Validation of a Peptide-Stabilized Poly(lactic-coglycolic) Acid Nanoparticle for Targeted Delivery of a Vascular Disruptive Agent in Cancer Therapy; Bioconjugate Chem.; Nov. 11, 2022; pp. 2348-2360; vol. 33; https://doi.org/10.1021/acs.bioconjchem.2c00418.

Huang, W. et al.; Tuning the Size of Poly(lactic-co-glycolic Acid) (PLGA) Nanoparticles Fabricated by Nanoprecipitation; Biotechnol. J.; 2018; 8 pages; vol. 13; DOI: 10.1002/biot.201700203.

Dragulska, Sylwia; Engineering and validation of peptide-stabilized nanomaterials for drug delivery and cancer therapy; ACS Conference Abstract; Mar. 21, 2022; San Diego, 1-page.

Acota-Santiago, Maxier; Developing mitochondria-targeting polymeric nanoparticles using peptides as non-covalent stabilizers; ACS Conference Abstract; Mar. 20, 2022; San Diego, 1-page.

Acota-Santiago, Maxier; Developing mitochondria-targeting polymeric nanoparticles using peptides as non-covalent stabilizers; Poster Presentation; ACS Conference; Mar. 20, 2022; San Diego, 1-page.

Poursharifi, Mina; Dissertation Abstract; Synthesis, characterization and applications of peptide-coated nanoparticles; Sep. 2021, 2-pages.

Dragulska, S. et al.; Engineering and validation of peptide-stabilized nanomaterials for drug delivery and cancer therapy; ACS presentation; Mar. 21, 2022; San Diego, 17-pages.

Dragulska, S. et al.; The development of pH-responsive peptide-coated nanoparticles for targeting and drug delivery to ovarian cancer cells; ACS Conference Abstract; Mar. 20, 2022; San Diego, 1-page.

Poursharifi, M. et al.; The development of peptide-coated nanoparticles for targeting and drug delivery to cancer cells; The FASEB Journal Abstract; Apr. 16, 2020; 2 pages; vol. 34, Issue S1; https://doi.org/10.1096/fasebj.2020.34. s1.02042.

Dragulska, S. et al.; Peptide-stabilized nanomaterials for drug delivery and cancer therapy; The FASEB Journal Abstract; Apr. 16, 2020; 2 pages; vol. 34, Issue S1.

(Continued)

*Primary Examiner* — Tigabu Kassa
*Assistant Examiner* — Ivan A Greene
(74) *Attorney, Agent, or Firm* — Schmeiser Olsen, PLLC; Peter J. Mikesell

(57) ABSTRACT

A method for forming peptide-coated nanoparticles. The nanoparticles are polylactic co-glycol polymer (PLGA). The coatings are self-assembled layers selected from RGDFFF (SEQ ID NO: 1); NGRFFF (SEQ ID NO: 2), EKHFFF (SEQ ID NO: 3) or TPP-KFF. A cargo molecule, such as a dye or a therapeutic may be bound to the nanoparticle.

10 Claims, 21 Drawing Sheets
(3 of 21 Drawing Sheet(s) Filed in Color)

Specification includes a Sequence Listing.

(56) References Cited

PUBLICATIONS

Dragulska, S. et al.; The development of pH-responsive peptide-coated nanoparticles for targeting and drug delivery to ovarian cancer cells; ACS conference poster presentation; Mar. 20, 2022; San Diego, 1-page.

Dragulska, S. et al.: Tripeptide-Stabilized Oil-in-Water Nanoemulsion of an Oleic Acids-Platinum(II) Conjugate as an Anticancer Nanomedicine; Bioconjug Chem.; Aug. 15, 2018; pp. 2514-2519; 29(8); doi:10.1021/acs.bioconjchem.8b00409 , 14-pages, as provided.

Slyngborg, M. et al.; The Physical Properties and Self-Assembly Potential of the RFFFR Peptide; ChemBioChem; 2016; pp. 2083-2092; vol. 17; DOI: 10.1002/cbic.201600383.

Cheetham A. et al.; Targeting Tumors with Small Molecule Peptides; Curr Cancer Drug Targets.; 2016; pp. 489-508; 16(6); doi:10.2174/1568009616666151130214646, 38-pages, as provided.

Danhier, F. et al.; PLGA-based nanoparticles: An overview of biomedical applications; Journal of Controlled Release; Feb. 4, 2012; pp. 505-522; 1vol. 21.

Branco, M. et al.; Materials from peptide assembly: towards the treatment of cancer and transmittable disease; Current Opinion in Chemical Biology; Apr. 18, 2011; pp. 427-434; vol. 15; DOI 10.1016/j.cbpa.2011.03.021.

Ndinguri, M. et al.; Peptide Targeting of Platinum Anti-Cancer Drugs; Bioconjug Chem.; 2009; pp. 1869-1878; vol. 10; doi:10.1021/bc900065r, 27-pages, as provided.

Borrelli, A. et al.; Cell Penetrating Peptides as Molecular Carriers for Anti-Cancer Agents; Molecules; Jan. 31, 2018; 28 pgs; vol. 23, Issue 295; doi:10.3390/molecules23020295.

* cited by examiner

| | HUVEC | OVCAR-3 | TOV-21G | ES-2 | OV-90 | SKOV-3 | A2780 | CP70 |
|---|---|---|---|---|---|---|---|---|
| RGDFFF (SEQ ID NO: 1) NPs | 93.8±5.0 | 14.9±3.6 | 34.9±27.9 | 66.1±9.4 | 19.0±11.0 | 25.0±8.0 | 25.6±8.2 | 22.9±18.0 |

FIG. 7A
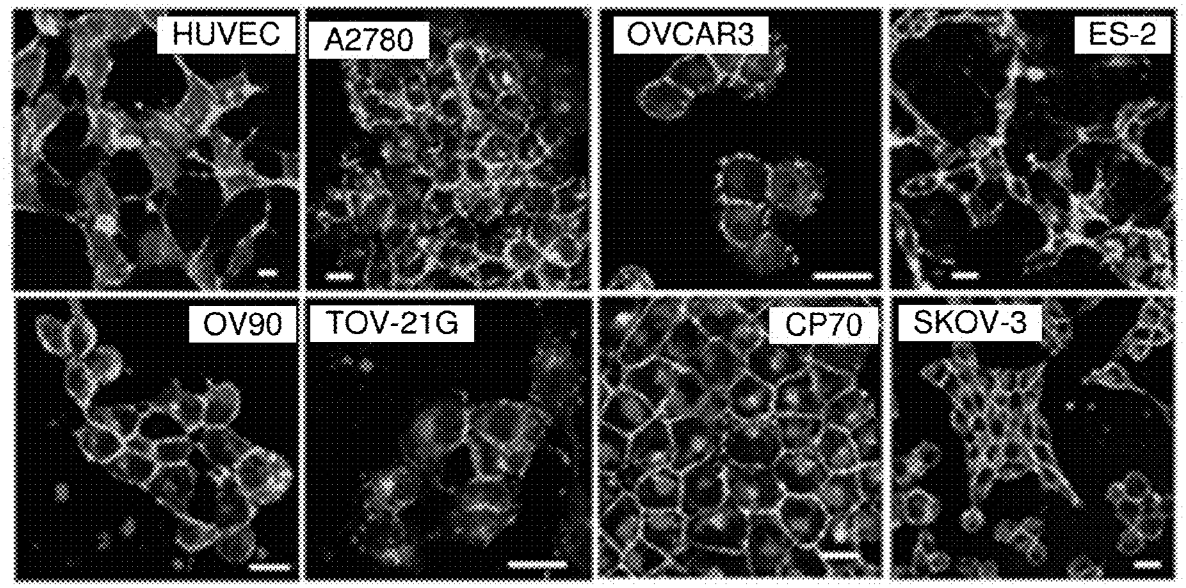
RGDFFF (SEQ ID NO: 1)-Cy5.5 NP uptake over time
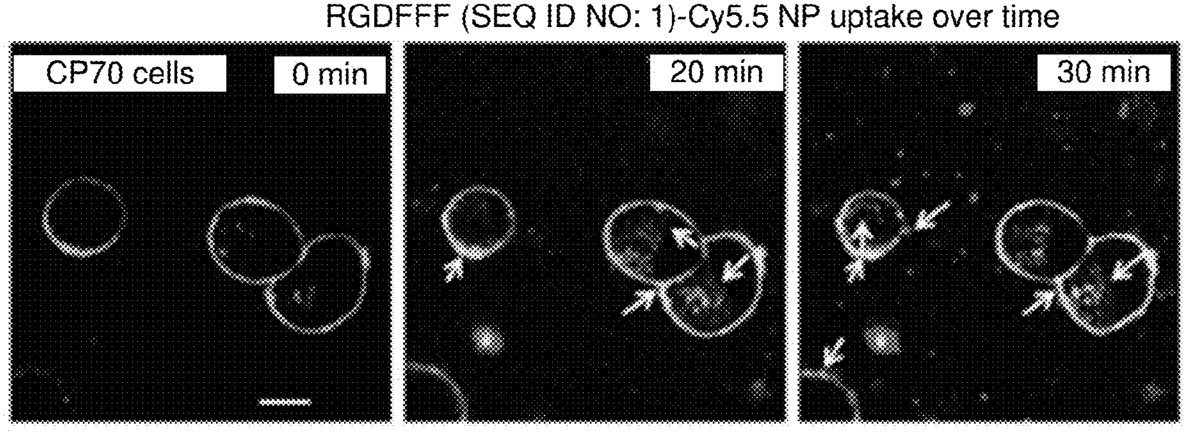
FIG. 7B Distribution of RGDFFF (SEQ ID NO: 1)-Cy7 NPs within the tumor tissue

| PT217 | PT927 | PT1264 | PT1310 | PT1315 | PT1332 |
|---|---|---|---|---|---|
| 67.4±8.3 | 66.8±6.2 | 52.8±2.5 | 91.3±1.6 | 63.6±17.3 | 70.9±12.9 |

METHOD OF FORMING PEPTIDE-COATED NANOPARTICLES

CROSS-REFERENCE TO RELATED APPLICATIONS

This application claims priority to, and is a non-provisional of, U.S. Patent Application 63/383,143 (filed Nov. 10, 2022), the entirety of which is incorporated herein by reference.

STATEMENT OF FEDERALLY SPONSORED RESEARCH OR DEVELOPMENT

This invention was made with Government support under grant number R01CA238539 awarded by the National Cancer Institute. The government has certain rights in the invention.

REFERENCE TO A SEQUENCE LISTING

This application contains a Sequence Listing in computer readable form. The computer readable form is incorporated herein by reference. The computer readable file is named Sequence.xml and was created on Nov. 8, 2023 (4 kB).

BACKGROUND OF THE INVENTION

Surface-coated nanoparticles are useful in treating a variety of medical conditions. However, to be useful to treat biological cells, such particles should be nanosized (e.g. ≤100 nm), spherical and uniform to enable permeation of the cell membrane.

Some peptide-coated PLGA particles have potential medical uses. Unfortunately, conventional nanoparticle formulation methods could not successfully produce nanoparticles for these formulations. Conventional methods inadvertently caused nanoparticle aggregation followed by precipitation of the aggregates. This, in turn, produces particles with diameters in the micrometer range. An improved method of nanoparticle formation is therefore desired.

The discussion above is merely provided for general background information and is not intended to be used as an aid in determining the scope of the claimed subject matter.

SUMMARY

This disclosure provides a method for forming peptide-coated nanoparticles. The nanoparticles are polylactic co-glycol polymer (PLGA). The coatings are self-assembled layers selected from RGDFFF (SEQ ID NO: 1); NGRFFF (SEQ ID NO: 2), EKHFFF (SEQ ID NO: 3) or TPP-KFF. A cargo molecule, such as a dye or a therapeutic may be bound to the nanoparticle.

In a first embodiment, a method for synthesizing a nanoparticle is provided. The method comprising sequential steps of: diluting a hexapeptide in nanopure water to a concentration between 0.1 mg per mL and 0.25 mg per mL, wherein the hexapeptide is selected from a group consisting of EKHFFF, NGRFFF and RGDFFF thereby producing a diluted hexapeptide solution; adding a solution of PLGA in acetonitrile dropwise at a rate of between 0.05 mL per min and 0.5 mL per min to the diluted hexapeptide solution while maintaining the diluted hexapeptide solution at a temperature of 37±3° C. for EKHFFF, NGRFFF and RGDFFF, wherein a total mass of the hexapeptide and a total mass of the PLGA are present in a mass ratio of 1:5 for EKHFFF or NGRFFF or a mass ratio of 1.5:5 for RGDFFF; stirring for at least 10 hours at a temperature between 20° C. and 25° C. to produce a raw solution; and dialyzing the raw solution to remove contaminates, thereby producing nanoparticles with a diameter of ≤100 nm.

In a second embodiment, a method for synthesizing a nanoparticle is provided. The method comprising sequential steps of: diluting a TPP-coupled tripeptide in nanopure water to a concentration between 0.1 mg per mL and 0.25 mg per mL, wherein the TPP-coupled tripeptide is TPP-KFF, wherein TPP is a (3-carboxypropyl)triphenylphosphonium salt; thereby producing a diluted TPP-coupled tripeptide solution; adding a solution of PLGA in acetonitrile dropwise at a rate between 0.05 mL per min and 0.5 mL per min to the diluted TPP-coupled tripeptide solution while maintaining the diluted TPP-coupled tripeptide solution at a temperature of 22±3° C. wherein a total mass of the TPP-coupled tripeptide and a total mass of the PLGA are present in a mass ratio of 1:5; stirring for at least 10 hours at a temperature between 20° C. and 25° C. to produce a raw solution; and dialyzing the raw solution to remove contaminates, thereby producing nanoparticles with a diameter of 100 nm.

In a third embodiment, a nanoparticle is provided. The nanoparticle comprising: a core of poly(lactic-co-glycolic) acid (PLGA) with a molecular weight selected from a group consisting of: 5 kDa to 10 kDa, 7 kDa to 17 kDa, and 30 kDa to 60 kDa; a peptide layer bound to the core in a coating thickness of between 2 nm and 3 nm, the peptide layer consisting of TPP-KFF, wherein TPP is a triphenylphosphonium salt; and a therapeutic agent covalently bound to the core at a concentration of at least 0.2% by mass; wherein the nanoparticle has a diameter of ≤100 nm.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 7A and FIG. 7B show cellular internalization of RGDFFF (SEQ ID NO: 1)-Cy5.5 NPs (red) in OvCA cell lines after 48 h incubation. The membrane (green) was stained with Alexa fluor 488-WGA, and the nucleus (blue) was labeled with DAPI. The scale bars are 20 μm. Bottom: Time-lapse images of RGDFFF (SEQ ID NO: 1) NPs (red) uptake by CP70 cells during the first 30 min of incubation. Arrows point to the NPs. The cellular membrane (green) was stained as above. The scale bar is 10 μm.

DETAILED DESCRIPTION OF THE INVENTION

This disclosure provides a method of producing polymeric nanoparticles (NPs) coated with short peptide sequences. A repeated L-Phenylalanine sequence (FF) provides a hydrophobic motif that allows for self-assembly to a nanoparticle. A hydrophilic motif in the peptide sequence acts as an active targeting or charge modulation on the NPs surface. The NP core is biocompatible and biodegradable polylactic co-glycol polymer (PLGA). All nanoparticle components are biologically safe and degraded to small molecule (such as amino acids, lactic and glycolic acid) that can be easily removed from the body. The nanoparticles represent good biological and colloidal stability, small size, and regular, spherical morphology that enhance using it for diagnosis and therapy applications.

Figure 1:
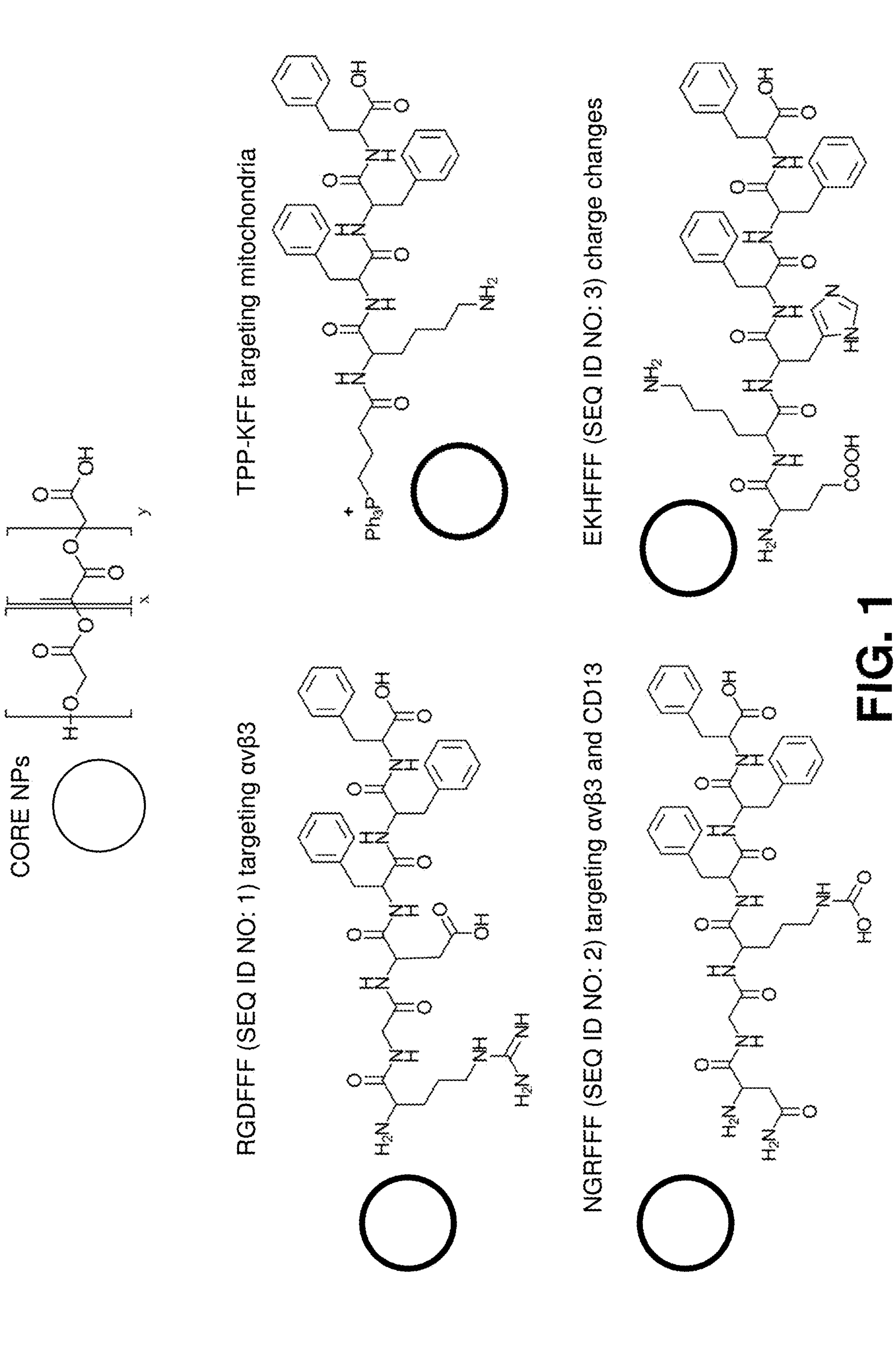
FIG. 1 depicts a scheme of peptide sequence and core structure used in nanoparticle (NP) synthesis.

Referring to FIG. 1, the two main components of the NPs are the core and a developed coating. The developed coating provides targeting while aggregating onto the NP-core via noncovalent interactions. The separate malleable pieces lead to an array of combinations to finetune the nanoparticle for the chosen application.

The coating uses peptide sequences designed to have two prominent motifs. By design, one motif is hydrophobic (e.g. FFF) and interacts with the hydrophobic PLGA core. The other motif is a hydrophilic motif that provides a specific property. This hydrophilic motif may enable a targeted strategy. Hydrophilic motifs of RGD and NGR αvβ3-expressing ovarian cancer (OvCA) cells are targeted. The NGR motif also targets CD13. The EKH sequence modifies the NP surface charge by responding to environmental pH, and triphenylphosphonium (TPP) targets the mitochondrion. The exploration of the noncovalent stabilizing peptide sequences has shown significant potential for flexibility for NP applications.

| Primary structure | SEQ ID NO: | Resulting property |
|---|---|---|
| RGDFFF | SEQ ID NO: 1 | Targets avß3-expressing ovarian cancer |
| NGRFFF | SEQ ID NO: 2 | Targets avß3-expressing ovarian cancer and CD13 |
| EKHFFF | SEQ ID NO: 3 | Changes change with pH |
| TPP-KFF | n/a | Targets mitochondria |

Example of synthesis of plain PLGA NPs. PLGA (5 mg, 0.0013 mmol, 1-5 kDa) in 2 mL of acetonitrile was added dropwise using a syringe pump (0.2 mL/min flow) into 6 mL of nanopure water at 37° C. Next, the PLGA-NPs were stirred overnight. After that, the NPs were concentrated in Vivaspin centrifugal concentrator (100 k MWCO) and washed 3 times with nanopure water. The PLGA is generally selected from 1-5, 5-10, 7-17 or 30-60 kDa average molecular weights. For better loading of cargo molecules, the shorter PLGA is recommended. For ease of precipitation, the longer PLGA is recommended.

Example of peptide synthesis: RGDFFF (SEQ ID NO: 1); NGRFFF (SEQ ID NO: 2) or EKHFFF (SEQ ID NO: 3). The following synthesis produces SEQ ID NO: 1 as an example. SEQ ID NO: 2 and 3 were synthesized with corresponding protocols.

A solid phase peptide synthesis (SPPS) method was used to synthesize a RGDFFF (SEQ ID NO: 1) peptide. Fmoc-L-Phe 4-alkoxybenzyl alcohol resin (0.5 g, 0.388 meq/g) was soaked in 25 mL of DMF for 1 h in a reaction vessel. Next, the amine group of L-phenylalanine amino acid 4-alkoxybenzyl alcohol resin was deprotected with 20% piperidine in DMF solution for 5 min followed by 20 min oscillation cycle. After deprotection, the resin was washed for 1 min with DMF and 1 min with isopropyl alcohol (IPA); each a total of three times. The Kaiser test was performed to determine the presence of free $NH_2$ group. If free $NH_2$ groups were detected, the coupling with Fmoc-L-phenylalanine amino acid was performed overnight (e.g. at least 10 hours). The following standard coupling conditions were used to attach each amino acid: Wang resin 0.19 mmol, Fmoc protected amino acid (0.38 mmol), TBTU 122.3 mg (0.38 mmol) and DIPEA 98.4 mg (0.76 mmol). The amino acids were dissolved with TBTU in DMF and DIPEA. The resin was washed with DMF, and IPA two times for 1 min each, followed by the Kaiser test. After coupling all amino acids, the resin was washed with 5 mL of DMF, IPA, DMF, methanol, dichloromethane and diethyl ether for 1 min each. The cleavage of RGDFFF (SEQ ID NO: 1) from the resin was achieved with a TFA/TIPS/$H_2O$ solution at a ratio of 95/2.5/2.5 for 3 hours. The crude peptide was precipitated in cold diethyl ether, washed 3 times with cold ether and then dried under vacuum. The product was washed with 10% HCl three times and dried. The peptide was purified by HPLC.

Example of coating of NP with a hexapeptide: The parameters of the PLGA peptide-coated NP formulation must be controlled precisely. Those include the temperature of the self-assembly process, concentrations of each component, order of addition, stirring rate, flow rate, and purification and concentration technique. Traditional protocols for making polymeric nanoparticles were incapable of producing stable peptide-coated nanoparticles such as EKHFFF (SEQ ID NO: 3), NGRFFF (SEQ ID NO: 3), RGDFF (SEQ ID NO: 1), or TPP-KFF.

A hexapeptide (RGDFFF (SEQ ID NO: 1); NGRFFF (SEQ ID NO: 2) or EKHFFF (SEQ ID NO: 3)) was diluted in nanopure water to a concentration between 0.1 mg per mL and 0.25 mg per mL. For EKHFFF (SEQ ID NO: 3 the concentration was 0.17 mg per mL. For NGRFFF (SEQ ID NO: 2), the concentration was 0.25 mg per mL. For RGDFFF (SEQ ID NO: 1) the concentration was 0.1 mg per mL. The resulting solution was warmed to 37±3° C. while stirring. A solution of 5 mg PLGA (or PLGA-cargo hybrid) was prepared in 3 mL acetonitrile. This solution was added dropwise at a rate of between 0.05 mL per min and 0.5 mL per min (e.g. 0.1 mL per min) to the diluted hexapeptide solution while stirring (700-1000 rpm). The diluted hexapeptide solution was maintained at a temperature of 37±3° C. The total mass of the hexapeptide and total mass of the PLGA are present in a mass ratio of 1:5 for EKHFFF (SEQ ID NO: 3) or NGRFFF (SEQ ID NO: 2) or a mass ratio of 1.5:5 for RGDFFF (SEQ ID NO: 1). The synthesis performed out of the temperature range cause nanoparticle aggregation followed by precipitation within 0-24 hours. Precipitation increases the nanoparticle hydrodynamic diameter from around 100 nm to micrometer range. The solution was then stirred (200 rpm) for at least 10 hours while maintaining a temperature between 20° C. and 25° C. to produce a raw solution. Organic solvents were allowed to evaporate during this time. The evaporation of the organic solvent overnight is a significant step in the synthesis of the coated NPs. This step is significant because slow evaporation of organic solvent: (1) decreases cytotoxicity of the nanoparticles in in-vitro and in-vivo steps by removal of acetonitrile (2) increases the stability of the nanoparticles maintaining their size and shape (see Biotechnol. J. 2018, 13, 1700203) and (3) increases the efficiency of the technological process of purification and concentration of the nanoparticles in the filter. The raw solution was subjected to dialysis (membrane 3.5 kDa) with nanopure water overnight (changing the water at least four times) while stirring. The solution was then washed three times with nanopure water and concentrated to a volume of 1 mL to provide a NP suspension. The suspension was stored at 4° C.

Example of synthesis of RGDFFF (SEQ ID NO: 1) NPs. PLGA (5 mg, 0.0013 mmol, 1-5 kDa) in 2 mL of acetonitrile was added dropwise using a syringe pump (0.2 mL/min flow) into RGDFFF SEQ ID NO: 1) peptide (1.5 mg, 0.0019 mmol) in 6 mL of nanopure water at 37° C. The solution was stirred overnight to allow the self-assembly of the RGDFFF (SEQ ID NO: 1) NPs. After that, the NPs were concentrated in Vivaspin centrifugal concentrator (100 k MWCO) and washed three times with nanopure water.

Example of synthesizing TPP-KFF: A resin of a fluorenylmethoxycarbonyl (Fmoc)-L-Phe 4-alkoxybenzyl alcohol was soaked in dimethylforamide (DMF) for at least thirty minutes. The resin was deprotected by removing the Fmoc group. The resulting suspension was then sequentially washed the resin with DMF, isopropyl alcohol (IPA), DMF and IPA for at least 1 minute each. A coupling mixture comprising at least two equivalents of an Fmoc-protected L-phenylalanine (Fmoc-F), 2 equivalents of 2-(1H-Benzotriazole-1-yl)-1,1,3,3-tetramethylaminium tetrafluoroborate (TBTU), and 4 equivalents of N,N-Diisopropylethylamine (DIPEA) in DMF was added to the washed, deprotected Phe-resin. Coupling was permitted to occur either (1) waiting for at least 10 hours at a temperature between 20° C. and 25° C. or (2) incubating for 10 minutes at 85° C. in a microwave. The resin may be subjected to a second round of deprotection and coupling to produce a FF dipeptide.

A coupling mixture comprising at least two equivalents of a Fmoc-protected L-lysine (Fmoc-K), 2 equivalents of 2-(1H-Benzotriazole-1-yl)-1,1,3,3-tetramethylaminium tetrafluoroborate (TBTU), and 4 equivalents of N,N-Diisopropylethylamine (DIPEA) in 2 mL of DMF was added to the washed, deprotected FF dipeptide. Coupling was permitted to occur by either (1) waiting for at least 10 hours at a temperature between 20° C. and 25° C. or (2) incubating for 10 minutes at 85° C. in a microwave, such that a tripeptide with a primary structure of KFF is produced.

A second coupling mixture comprising at least two equivalents of (3-carboxypropyl)triphenylphosphonium bromide (TPP), at least two equivalents of 2-(1H-Benzotriazol-1-yl)-1,1,3,3-tetramethyluronium hexafluorphosphate (TBTU) and at least four equivalents of N,N-Diisopropylethylamine (DIPEA) in 2 mL DMF was added to the washed and deprotected tripeptide KFF. Coupling is permitted to occur by either (1) waiting for at least 10 hours at a temperature between 20° C. and 25° C. or (2) incubating for 10 minutes at 85° C. in a microwave, such that a resin-bound TPP-KFF is formed. This resin-bound TPP-KFF is sequentially washed with DMF, IPA, DMF, IPA, DMF and DMF for at least 1 minute each. The TPP-KFF was then cleaved from the resin under acidic conditions, thereby forming TPP-KFF. The TPP-KFF may be precipitated in an organic solvent, such as cold methanol.

Example 1 of coating of NP with TPP-KFF: A TPP-KFF bromide was dissolved in nanopure water to a concentration between 0.1 mg per mL and 0.25 mg per mL (e.g. 0.1 mg per mL). A solution of PLGA in acetonitrile (e.g. 5 mg per 1.5 mL) was added dropwise at a rate between 0.05 mL per min and 0.5 mL per min to the diluted TPP-coupled tripeptide solution while maintaining a temperature of 22±3° C. and stirring (700-1000 rpm). The total mass of the TPP-coupled tripeptide and a total mass of the PLGA are present in a mass ratio of 1:5. The suspension was stirred for at least 10 hours at a temperature of 22±3° C. to produce a raw solution which was subsequently purified by dialysis.

Example 2 of coating of NP with TPP-KFF: A TPP-KFF bromide was dissolved in nanopure water to a concentration 0.1 mg per mL. A solution of PLGA (5 mg, 0.00167 mmol 1-5 kDa) in 1.5 mL acetonitrile was added dropwise at a rate of 0.1 mL per min to the diluted TPP-coupled tripeptide solution while maintaining a temperature of 22° C. and stirring (700 rpm). The total mass of the TPP-coupled tripeptide and a total mass of the PLGA are present in a mass ratio of 1:5. The suspension was stirred for at least 10 hours at a temperature of 22° C. to produce a raw solution which was subsequently purified by dialysis.

Cargo Molecules

A cargo molecule, such as a dye or therapeutic, may be bound to the NP. Examples of suitable dyes include Cy5.5, FITC, Cy7, Alexa-fluor dyes, AMCA, coumarin, TRITC, Rhodamine red, Texas Red, IR680 and the like. Examples of suitable therapeutics include combretastatin-A4 (CA4). The cargo molecule may be covalently bound to the PLGA with a peptide bond or an ester bond.

Example of synthesis of PLGA-Cy5.5 hybrid. PLGA-$NH_2$ (101 mg, 0.00363 mmol, MW 28000, PolySciTech) was dissolved in 2.5 mL of dry DMF and mixed with Cy 5.5-NHS ester (2.6 mg, 0.00363 mmol, Lumiprobe) dissolved in 0.5 mL of DMF. Triethylamine (10 μl) was added to the solution and the reaction mixture was stirred overnight. Then, DMF was removed under reduced pressure and crude reaction mixture was dissolved in 1 mL of acetonitrile. Product was precipitated out with cold methanol and stored in the fridge. The reaction provided 49.7 mg of blue solid (47% yield).

Example of synthesis of RGDFFF (SEQ ID NO: 1)-Cy5.5 NP. PLGA-Cy5.5 (1 mg) was dissolved in 0.1 mL acetonitrile and mixed with PLGA (4 mg, 0.00033 mmol 7-17 kDa) in 1.9 mL acetonitrile. The solution was added dropwise using a syringe pump (0.1 mL/min flow) into 1 mg (0.0013 mmol) of RGDFFF (SEQ ID NO: 1) peptide in 6 mL of nanopure water at 37° C. After that the solution was stirred overnight to allow the self-assembly of the RGDFFF (SEQ ID NO: 1)-Cy5.5 NPs. The RGDFFF (SEQ ID NO: 1)-PLGA-Cy 5.5 NPs were concentrated in Vivaspin centrifugal concentrator (100 k MWCO) and washed 3 times with nanopure water.

Example of synthesis of PLGA-Cy7 hybrid. 7 mg (0.0097 mmol) of Cy 7-NHS ester (Lumiprobe) were added to 200 mg (0.006 mmol) of 24-38 kDa PLGA, followed by the addition of 2.66 mg (0.013 mmol) of DCC and 3.33 mg (0.026 mmol) of DIPEA. All reagents were dissolved in DMF. Reaction mixture was gently stirred overnight at 4° C. Crude product was dried using rotary evaporator and dissolved in small amount (~1 mL) of acetonitrile. The product was added dropwise to cold methanol and kept at −20° C. overnight. Next, the product was centrifuged, and dissolved in acetonitrile. Last three steps were repeated 3 times to obtain the pure product. Finally, the product (dark blue) was dried in a lyophilizer. The yield of the reaction was established to be 72%.

Example of synthesis of plain RGDFFF (SEQ ID NO: 1)-Cy7 NPs. PLGA (4 mg, 0.00013 mmol, 24-38 kDa) and PLGA-Cy7 (1 mg, 0.0000323 mmol) were dissolved in 2 mL acetonitrile and added dropwise using a syringe pump (0.2 mL/min flow) into RGDFFF (SEQ ID NO: 1) peptide (1.5 mg, 0.0019 mmol) in 6 mL of nanopure water at 37° C. The solution was stirred overnight to allow the self-assembly of RGDFFF (SEQ ID NO: 1)-PLGA-Cy 7 NPs. After that the NPs were concentrated in Vivaspin centrifugal concentrator (100 k MWCO) and washed 3 times with nanopure water.

Combretastatin A4

In one embodiment, the cargo molecule is combretastatin A4 (CA4), the tubulin-binding agent. CA4 is one of the vascular disrupting agents in active development for ovarian cancer therapy. The CA4 mode of action involves tubulin binding near the colchicine binding site, which damages endothelial cell cytoskeleton and cell shape change, ultimately leading to compromising blood flow to the tumor and tumor necrosis. Although highly potent, CA4 is not soluble in water. Instead, a prodrug form (CA4-phosphate) must be used in clinical applications. However, the therapy with CA4-phosphate is associated with systemic toxicity, which include cardiovascular adverse events and hypertension.

Figure 2:
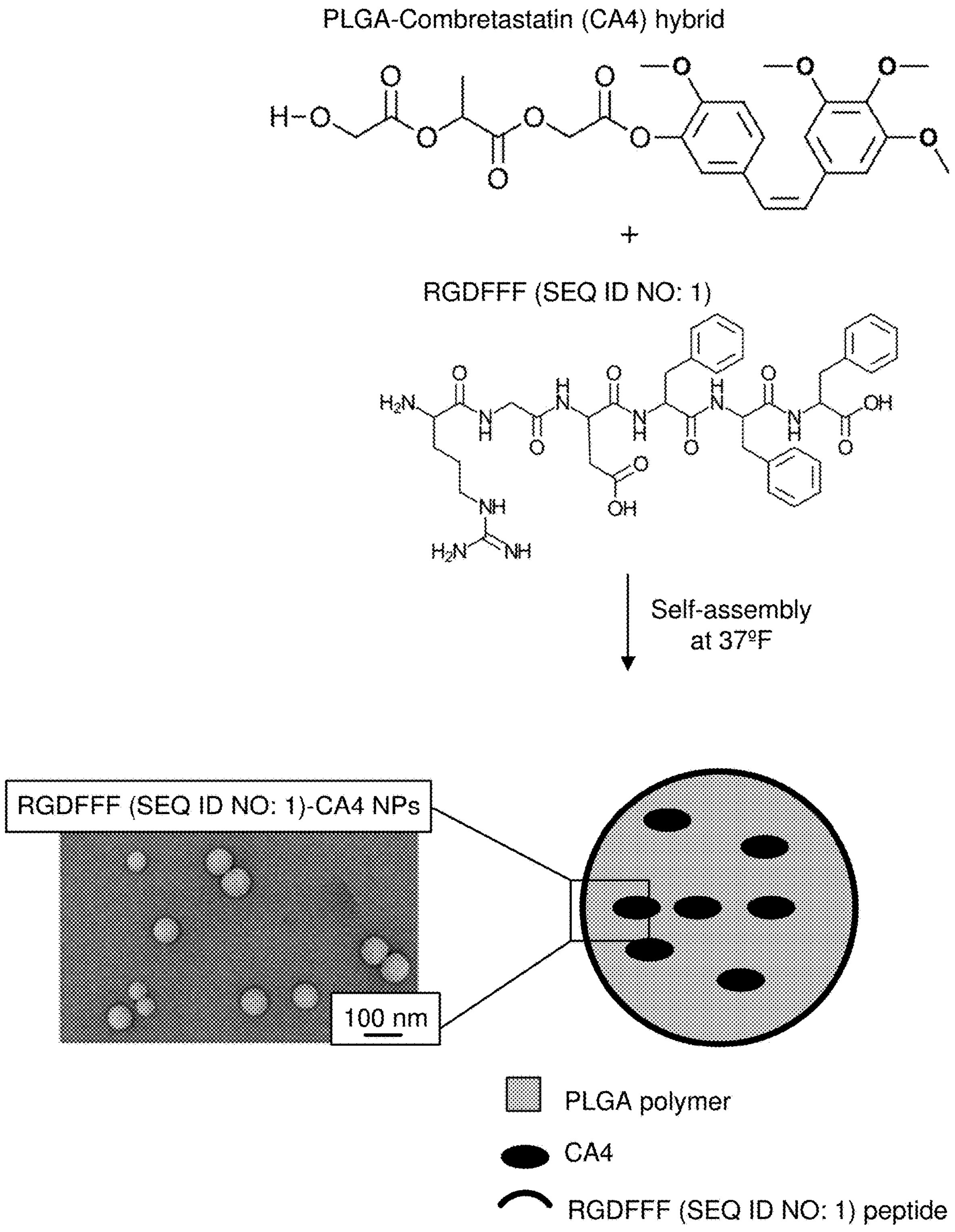
FIG. 2 is a schematic representation of PLGA-CA4 conjugate and RGDFFF (SEQ ID NO: 1) peptide and RGDFFF (SEQ ID NO: 1)-CA4 NP. The TEM image shows a large area with RGDFFF (SEQ ID NO: 1)-CA4 NPs.

CA4 was conjugated to PLGA polymer via an ester bond (FIG. 2) between the carboxyl group of PLGA and the hydroxyl group of CA4. The PLGA:CA4 ratio in the PLGA-CA4 hybrid was determined by HPLC and was found to be 90:1. The RGDFFF (SEQ ID NO: 1)-CA4 NP was formed using the disclosed nanoprecipitation method. To this end, the PLGA-CA4 conjugate in acetonitrile was added drop-wise to an aqueous solution of RGDFFF (SEQ ID NO: 1) peptide at 37° C., at a PLGA-CA4:RGDFFF (SEQ ID NO: 1) molar ratio of 1:1.5. The solution was stirred overnight allowing the self-assembly of the RGDFFF (SEQ ID NO: 1)-CA4 NPs. Next, the NPs were pre-concentrated and washed in a centrifugal concentrator. The schematic of PLGA-CA4 hybrid, as well as the RGDFFF (SEQ ID NO: 1) peptide, are shown in FIG. 2, and RGDFFF (SEQ ID NO: 1)-CA4 NP is also shown in FIG. 2 followed by a transmission electron microscopy (TEM) image of the NPs (bottom left).

The PLGA NPs are coated with a short peptide, RGDFFF (SEQ ID NO: 1), and encapsulated CA4 to target angiogenesis in cancer. The RGDFFF (SEQ ID NO: 1) peptide self-assembles on the PLGA surface due to the presence of the terminal phenylalanine (F) residues, which facilitate the process. The arginine-glycine-aspartic acid (RGD) moiety serves as a vascular and cancer-specific active targeting ligand. In other embodiments SEQ ID NO: 2, SEQ ID NO: 3 or TPP-KFF may be used. Importantly, one desirable feature of the NPs is complete biodegradability. PLGA is approved by the U.S. Food and Drug Administration (FDA) and the peptides are inherently biodegradable to amino acids that have generally regarded as safe (GRAS) status, which can collectively reduce barriers to clinical translation of the NPs.

Figure 3A:
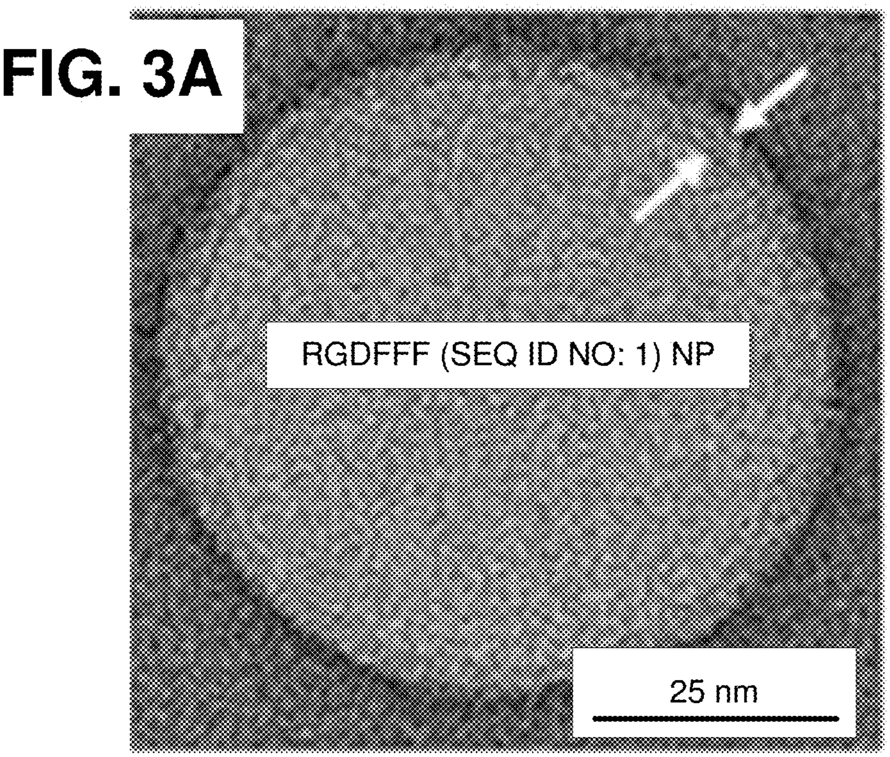
FIG. 3A is a TEM image of a RGDFFF (SEQ ID NO: 1) NP.
Figure 3B:
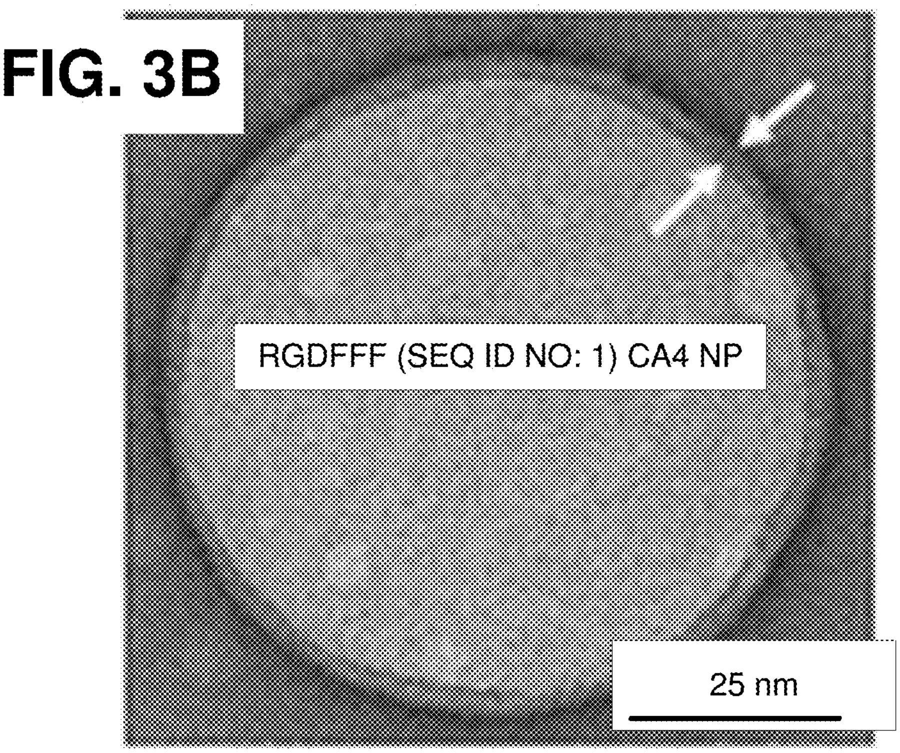
FIG. 3B is a TEM image of a RGDFFF-CA4 NP.
Figure 3C:
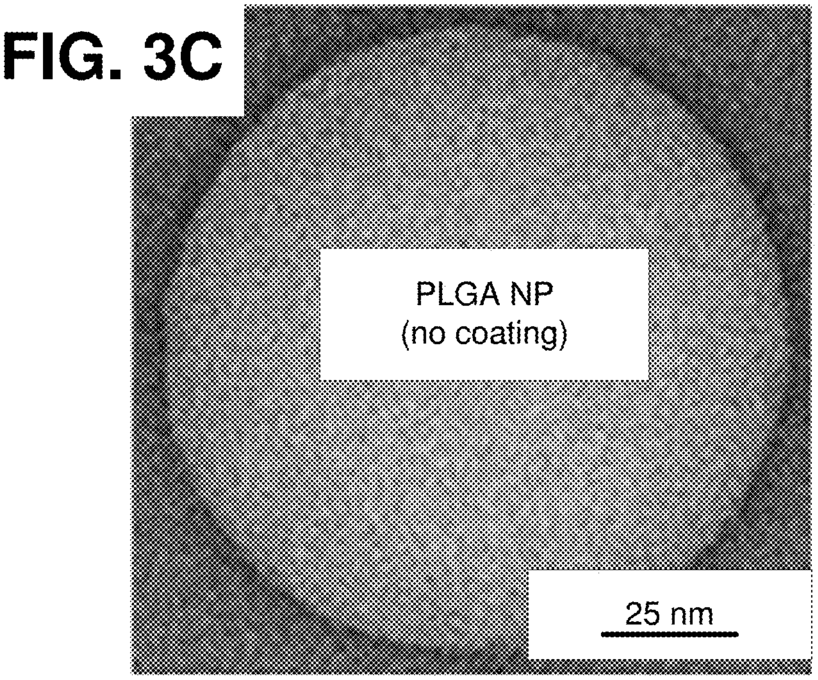
FIG. 3C is a TEM image of a plain PLGA NP (no coating).

The size, morphology, and the presence of the peptide shell on the NPs have been evaluated using TEM. The NPs were spherical in shape and the average diameter was 75±3.7 nm. This size allows NPs to accumulate in the interstitial tumor space through the enhanced permeability and retention (EPR) effect. The zoomed-in images of the empty RGDFFF (SEQ ID NO: 1, no drug), RGDFFF (SEQ ID NO: 1)-CA4, and PLGA NP are presented in FIG. 3A, FIG. 3B and FIG. 3C, respectively. The peptide coating is visible as a 2-3 nm rim on the RGDFFF (SEQ ID NO: 1)-NP's surface (FIG. 3A). Drug encapsulation did not noticeably affect the NP's morphology, and the peptide coating is apparent on the surface of RGDFFF (SEQ ID NO: 1)-CA4 NP (FIG. 3B). The thin layer was not present in the plain PLGA NP (FIG. 3C), suggesting that the coating formed from the RGDFFF (SEQ ID NO: 1)-peptide.

Figure 3D:
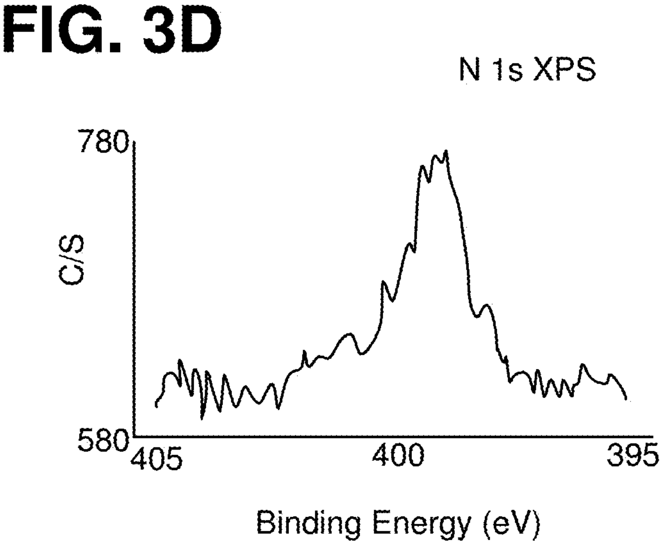
FIG. 3D is a XPS spectrum of RGDFFF (SEQ ID NO: 1)-PLGA NPs showing the peak of N 1s.

To confirm these findings, the empty RGDFFF (SEQ ID NO: 1)-NP (no drug) was further investigated by X-ray photoelectron spectroscopy (XPS), a surface-sensitive technique capable of providing the composition data of the uppermost 1-10 nm of the surface. The NPs were deposited on a Si wafer and analyzed for nitrogen presence; nitrogen can originate only from the peptide coating and is not present in the PLGA core. The XPS spectrum (FIG. 3D) of the NPs demonstrates a well-pronounced N is peak. This finding confirms that the NP's coating is the RGDFFF (SEQ ID NO: 1)-peptide. The overall elemental composition of the surface was 1.1% N, 66% C and 32.9% O in the RGDFFF (SEQ ID NO: 1)-NP.

The Zeta potential of the NPs was measured by dynamic light scattering at pH 7.4 and was found to be −44.2±4.1 mV, indicating negative surface charge and good colloidal stability. The measured negative surface charge agrees with the isoelectric point (pI) of the RGDFFF (SEQ ID NO: 1)-peptide, which is 5.84. Thus, at a pH higher than pI, the overall charge of the RGDFFF (SEQ ID NO: 1)-will be negative while positive at lower pH. This charge conversion could potentially contribute to greater NP uptake by negatively charged endothelial cells in the tumor tissue, where pH is lower than physiological levels. In addition, negatively charged NPs have prolonged circulating half-lives and reduced non-specific interactions with plasma proteins that may induce cytotoxicity.

Figure 4A:
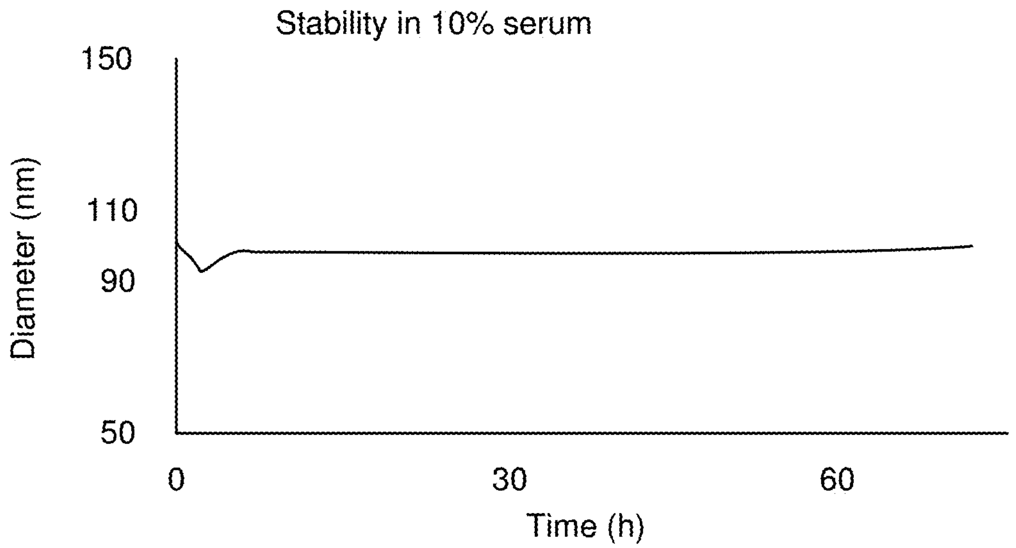
FIG. 4A is a graph showing the stability of RGDFFF (SEQ ID NO: 1)-CA4 NPs in 10% serum.

The RGDFFF (SEQ ID NO: 1)-CA4 NPs were also evaluated for stability in serum. In a test, 1 mg/ml of the NPs was suspended in 10% mouse serum. The NP's size was measured by DLS over time to determine any cluster formation and aggregation phenomena that would increase the size distribution of the NPs. The size did not vary for the NP preparation, as shown in FIG. 4A, indicating that the NPs do not opsonize in serum. Similarly, the NPs were stable in PBS.

Figure 4B:
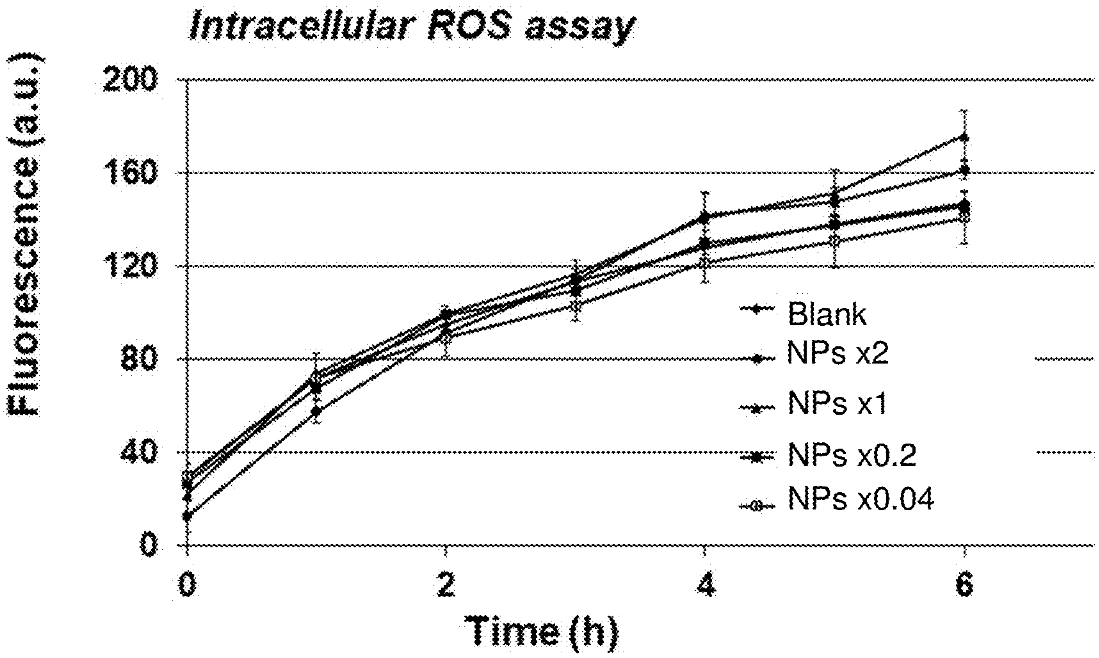
FIG. 4B is a graph showing intracellular production of ROS in the presence of RGDFFF (SEQ ID NO: 1) NPs in different concentrations. Error bars represent the mean±standard deviation of three independent trials.

The interactions between NPs and the innate immune system can induce diverse immunological responses and may lead to immunotoxicity. The RGDFFF (SEQ ID NO: 1)-NP platform (no drug) was evaluated for compatibility with the immune system using macrophage RAW 264.7 cells. Macrophage production of excessive reactive oxygen species (ROS) was measured and reactive nitrogen species (RNS) upon incubation with the NP. ROS/RNS are produced from cellular activity in the different organelles, such as mitochondria, endoplasmic reticulum (ER), and peroxisomes. These play a pivotal role in various cellular functions such as cellular growth, proliferation, and differentiation. However, an elevated ROS/RNS rate is hazardous and can cause damage to multiple cellular organelles and promote unregulated inflammation. To evaluate the effect of RGDFFF (SEQ ID NO: 1)-NP on ROS production, cells were exposed to different NP concentrations, where concentration ×1 corresponded to the theoretical plasma concentration of CA4 if the drug was to be present in the NP. The results are presented in FIG. 4B and show no differences between NP treated and blank control suggesting that the RGDFFF (SEQ ID NO: 1)-NP platform had no effect on ROS formation by the cells. Plain PLGA NPs had a similar effect on ROS production as RGDFFF (SEQ ID NO: 1)-NPs.

Figure 4C:
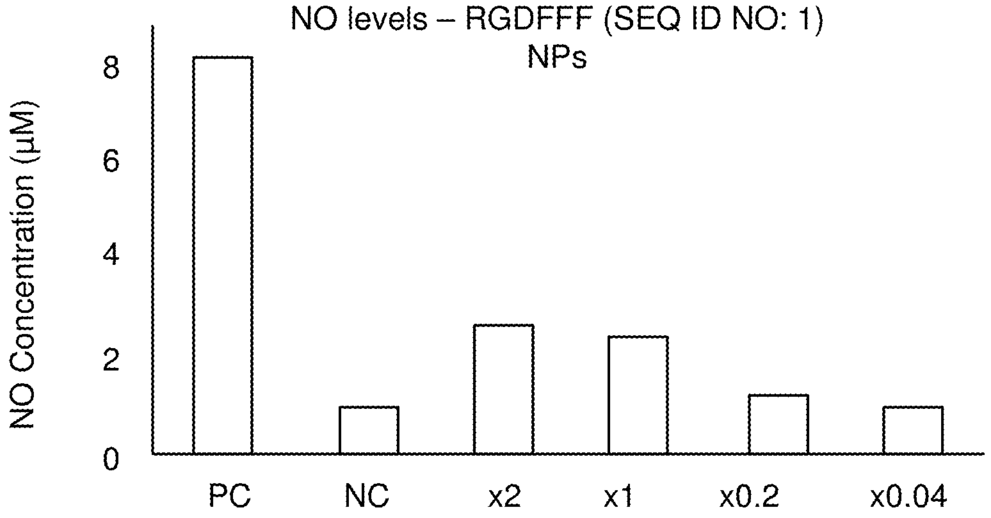
FIG. 4C and FIG. 4D are graphs showing NO production of RAW264.7 cell lines in the presence of RGDFFF (SEQ ID NO: 1) NPs (FIG. 4C) and plain (uncoated) PLGA NPs (FIG. 4D). In ROS and NO experiments, the concentrations of the NPs are as follows: ×2—0.034 mg/ml, ×1—0.017 mg/ml, ×0.2—0.0034 mg/ml, and ×0.04—0.00068 mg/ml. PC—positive control (100 ng/ml LPS), NC—negative control: untreated RAW264.7 cells (PBS).
Figure 4D:
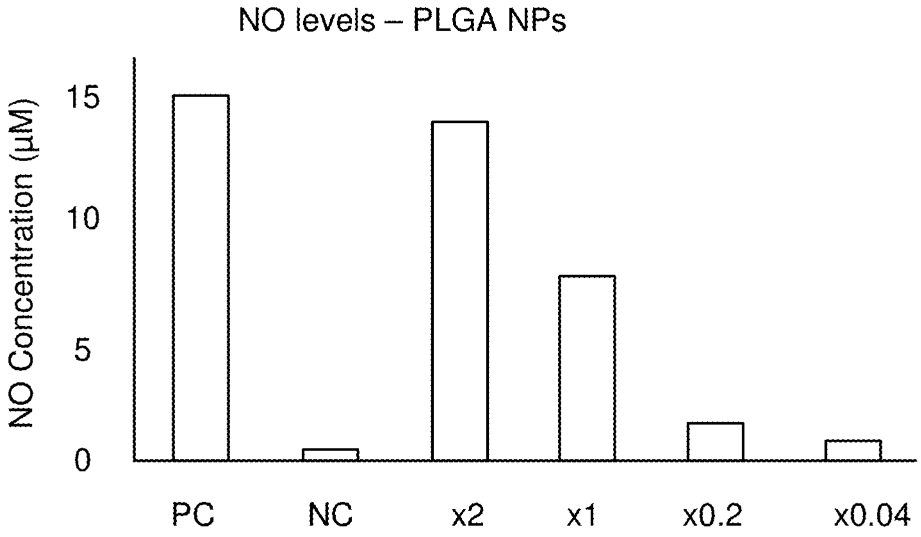

To assess RNS production NO levels were measured in the culture medium of RAW 264.7 cells incubated with the RGDFFF (SEQ ID NO: 1)-NPs at the same concentrations as in the ROS experiment. The values were compared with lipopolysaccharide (LPS) (positive control) and PBS (negative control). As shown in FIG. 4C, high nitric oxide levels in the presence of RGDFFF (SEQ ID NO: 1)-NPs were not detected. Interestingly, the effect of plain PLGA NP (no coating) on NO production was more pronounced (FIG. 4D), suggesting that the RGDFFF (SEQ ID NO: 1)-coating may diminish NP immunogenicity.

Figure 5:
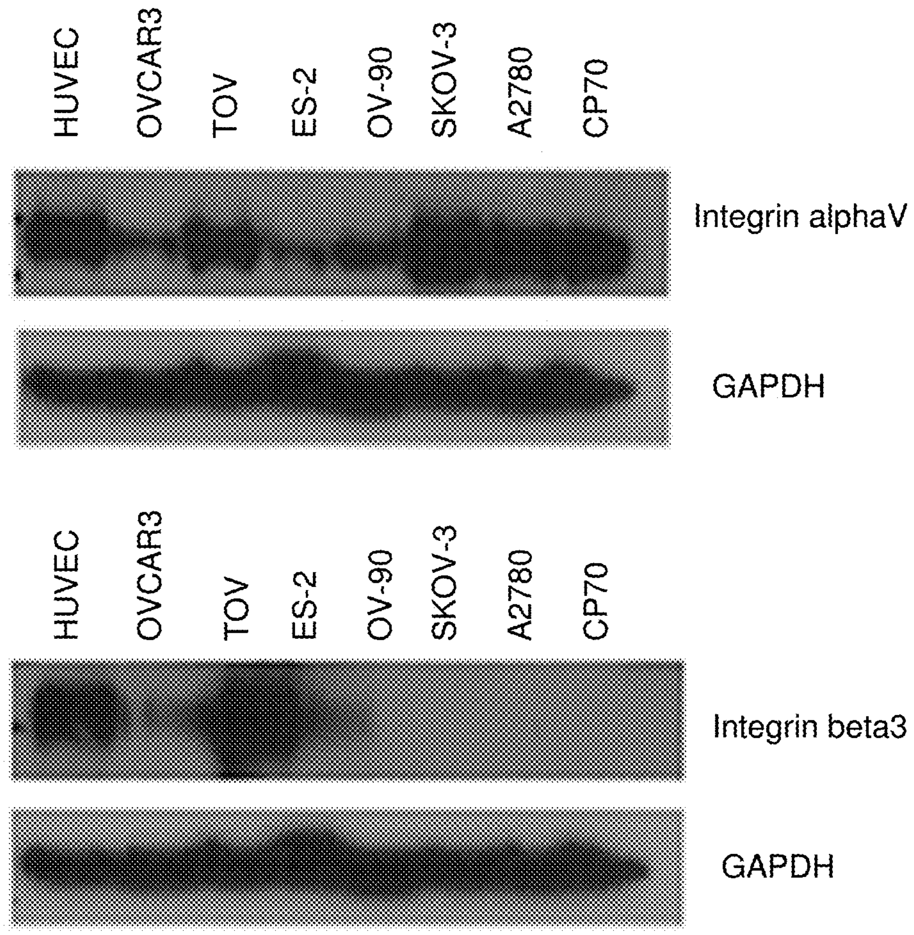
FIG. 5 are Western blots of HUVEC and various OvCA-relevant cell line lysates demonstrating expression of αv and β3 subunits. 80 μg of protein was loaded per lane. The panels shown are representative of N=3 independent trials.

As an introduction to biological applications of the RGDFFF (SEQ ID NO: 1)-CA4 NPs, the expression level of αvβ3 integrin in human umbilical vein endothelial cells (HUVEC) was established, representative of angiogenesis, as well as in selected OvCA cell lines. To this end, a Western blot test was used to verify the presence of αv and β3 integrins in HUVEC, and in an array of immortalized OvCA cell lines, including the isogenic A2780 and CP70 cell lines, and ES-2, OV-90, SKOV-3, OVCAR-3, TOV-21G cells, all with characterized genomic features and different histotype origins. GAPDH was used as a reference/housekeeping gene. All cells expressed αv integrin, with HUVEC, TOV-21G, SKOV-3, A2780, and CP70 cells showing slightly higher expression levels than OVCAR-3, ES-2, and OV-90 cells (FIG. 5). However, the expression of β3 integrin was more heterogeneous, and the highest signal was detected in HUVEC, as expected, and also in TOV-21G cells. Some signal was detected in other cell lines, such as OVCAR-3, and ES-2, while OV-90, SKOV-3, A2780, and CP70 cells expression was too low to detect.

Figure 6:
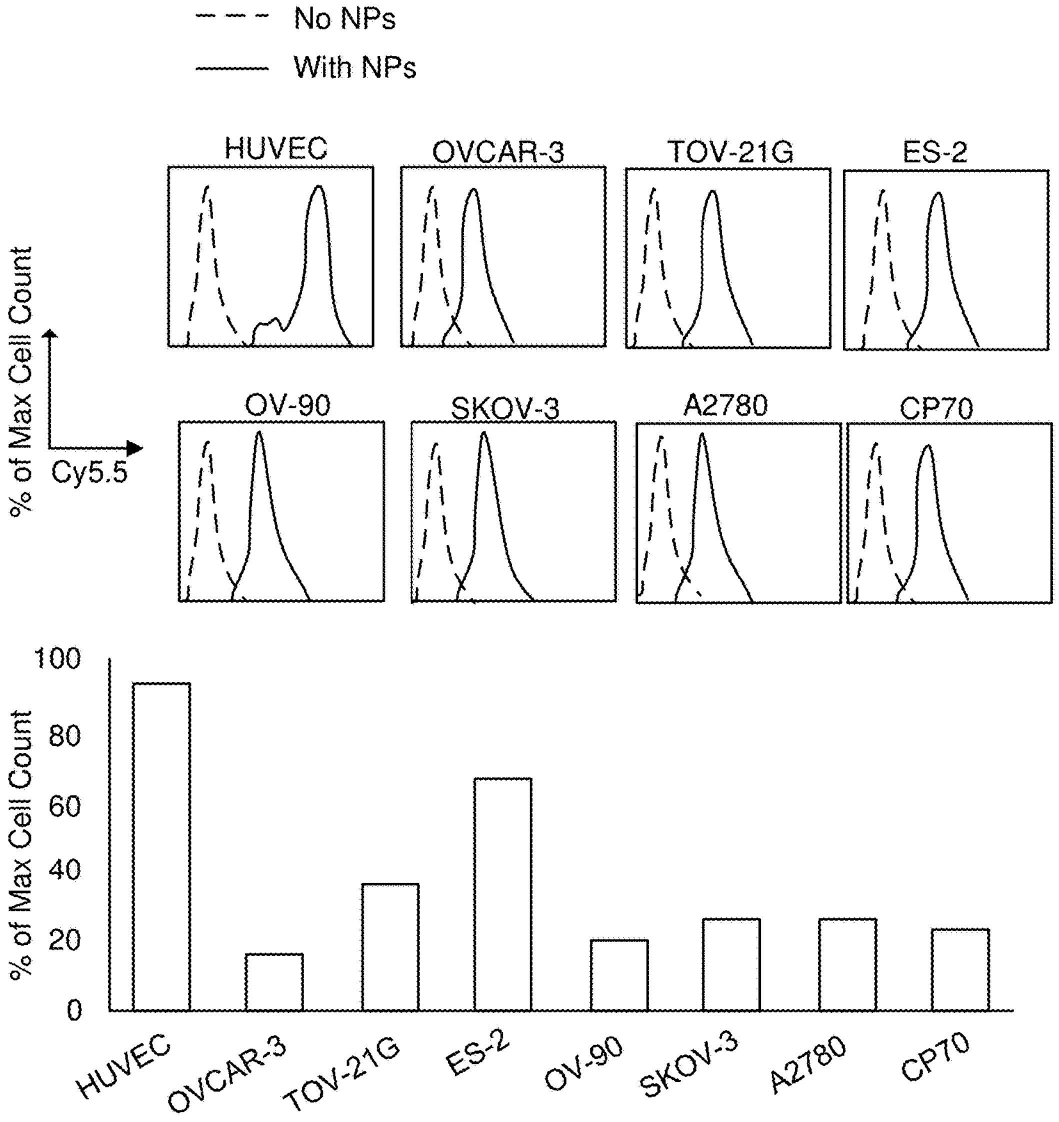
FIG. 6 is a graph showing the results of a flow cytometry analysis of RGDFFF (SEQ ID NO: 1)-Cy5.5 NP uptake. All cell lines were incubated with the NPs and harvested after 15 min. Control cells receiving no NPs, are shown with a dashed line, and cells treated with NPs are shown with a solid line. The table characterizes the percent of NP-positive cells.

The expression levels of αv and β3 subunits were correlated with the extent of NP uptake. To this end, fluorescent RGDFFF (SEQ ID NO: 1)-Cy5.5 NPs (no drug) was used, where PLGA was chemically modified with Cy5.5, and the ratio of PLGA:PLGA-Cy5.5 in the core was 4:1. The cells were incubated with RGDFFF (SEQ ID NO: 1)-Cy5.5 NPs for 15 min, washed, collected in suspension, and then examined by flow cytometry. The experiment was performed in triplicate, and representative results are shown in FIG. 6. Approximately 98.0% of HUVEC were demonstrated to have taken up the NP. The highest percent positivity in all other cell lines tested was observed in ES-2 (66.1%) and TOV-21G (46%) cells. This increased level corresponded to the high expression of both αV and β3 integrin subunits. Other OvCA cell lines were also positive for RGDFFF (SEQ ID NO: 1)-Cy5.5 NPs, even when the expression of β3 integrin subunit in the cells was below the detection limit. This might stem from the fact that the RGD motif was found to have an affinity to other integrin proteins as well, such as αVβ5 or α5β1. Therefore the direct comparison between single integrin expression and the NP's uptake is challenging.

To corroborate the RGDFFF (SEQ ID NO: 1)-Cy5.5 NP uptake by HUVEC and OvCA cells, the cells were imaged using LSM 880 Airyscan Fast Live Cell confocal microscope after 48 h incubation with the NPs. The NPs (red) are visible inside all cells tested (FIG. 7A), further suggesting that the NPs are internalized by the cells. Finally, NP entry into the cells was investigated using time-lapse microscopy. As shown in FIG. 7B, the NPs attach to the cell membranes of CP70 cells over the first 30 min after adding the RGDFFF (SEQ ID NO: 1)-Cy5.5 NPs and progressively accumulate inside the cells.

Figure 8:
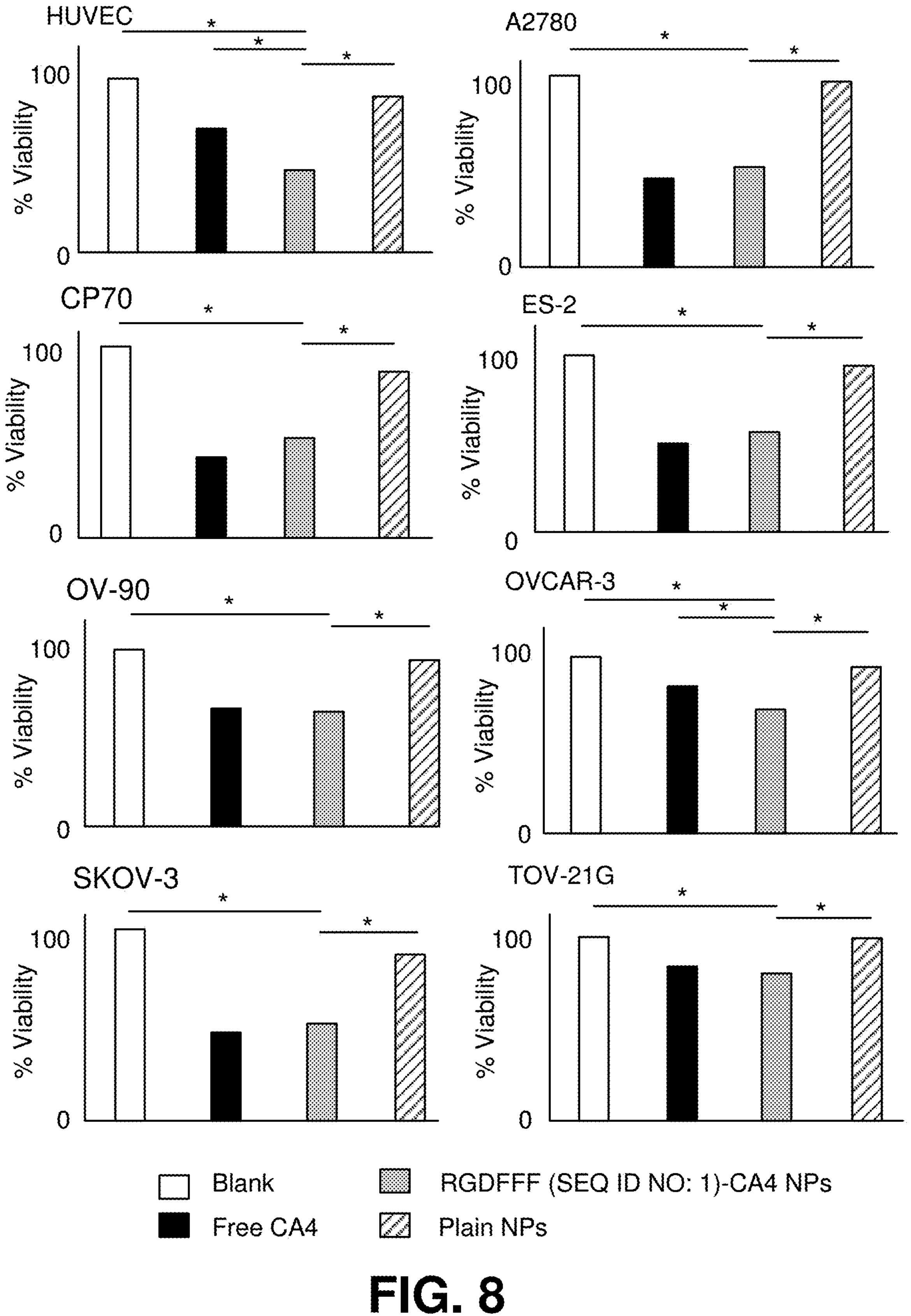
FIG. 8 depicts a series of graphs showing in vitro viability with RGDFFF (SEQ ID NO: 1)-CA4 NP. Each column represents the mean and standard deviation of N=3 and $p<0.005$ (HUVEC, OVCAR-3), $p<0.04$ (TOV-21G, OV-90), $p<0.03$ (CP70), $p<0.02$ (A2780), $p<0.01$ (ES-2), $p<0.12$ (SKOV-3). The concentrations correspond to $IC_{50}$ values of CA4 for each cell line and are as follows: 2 nM (HUVEC), 5 nM (A2780), 4 nM (CP70), 5 nM (ES-2), 100 nM (OV-90), 2.5 nM (OVCAR-3), 10 nM (SKOV-3), 25 nM (TOV-21G).

The biological activity of RGDFFF (SEQ ID NO: 1)-CA4 NPs in cell culture was also evaluated. As determined by HPLC, the CA4 drug payload in the NP was 0.2 wt. %. First, $IC_{50}$ values were established for the NPs in all cells and subsequently performed MTT viability assays in HUVEC and OvCA cells using the respective $IC_{50}$ values. The RGDFFF-CA4 NPs were compared to cells only without treatment, free CA4, and empty RGDFFF (SEQ ID NO: 1)-NPs without CA4, as shown in FIG. 8. RGDFFF (SEQ ID NO: 1)-CA4 NPs showed cytotoxic activity. The most pronounced effect was observed in HUVEC, the primary drug target for the NP, with 20% greater impact on viability when compared to free CA4. In OvCA cell lines, RGDFFF (SEQ ID NO: 1)-CA4 NPs lowered the cellular viability at levels comparable to free CA4. Optical microscopy was used to examine the morphological changes in the cells after incubation with RGDFFF (SEQ ID NO: 1)-CA4 NP. This was done since CA4 is a microtubule depolymerizing agent that disrupts internal cell architecture. Upon incubation with RGDFFF (SEQ ID NO: 1)-CA4 NP, cell morphology was visibly disrupted, changing from elongated and flat to rounded and bloated. The changes were suggestive of CA4 action and were also visible in cells incubated with free CA4. These results suggest that RGDFFF (SEQ ID NO: 1)-CA4 NP can be used as an efficient transport and drug delivery vehicle, acting upon vascular and OvCA cells.

As a prelude to in vivo biodistribution studies, the pharmacokinetic properties of the RGDFFF (SEQ ID NO: 1)-coated NPs (no drugs) were examined, where PLGA was modified with Cy7 near-infrared (NIR) fluorophore. In this experiment, the PLGA:PLGA-Cy7 at the ratio of 80:20 constituted the core of the NPs, where the Cy7 was chemically conjugated to the PLGA. NIR fluorescence was used to measure the concentration of the RGDFFF (SEQ ID NO: 1)-Cy7 NPs in the blood samples. Nude mice were IV dosed with NPs at a concentration of 2.66 mg/kg. This dose corresponds to NPs carrying a CA4 dose for patients (60 mg/m$^2$), converted to its equivalent dose for mice. Blood samples were drawn at 15, 30, and 90 min. After the experimental fitting of the data, the in vivo half-life of the RGDFFF (SEQ ID NO: 1)-Cy7 NPs was determined to be 45 min.

Figure 9:
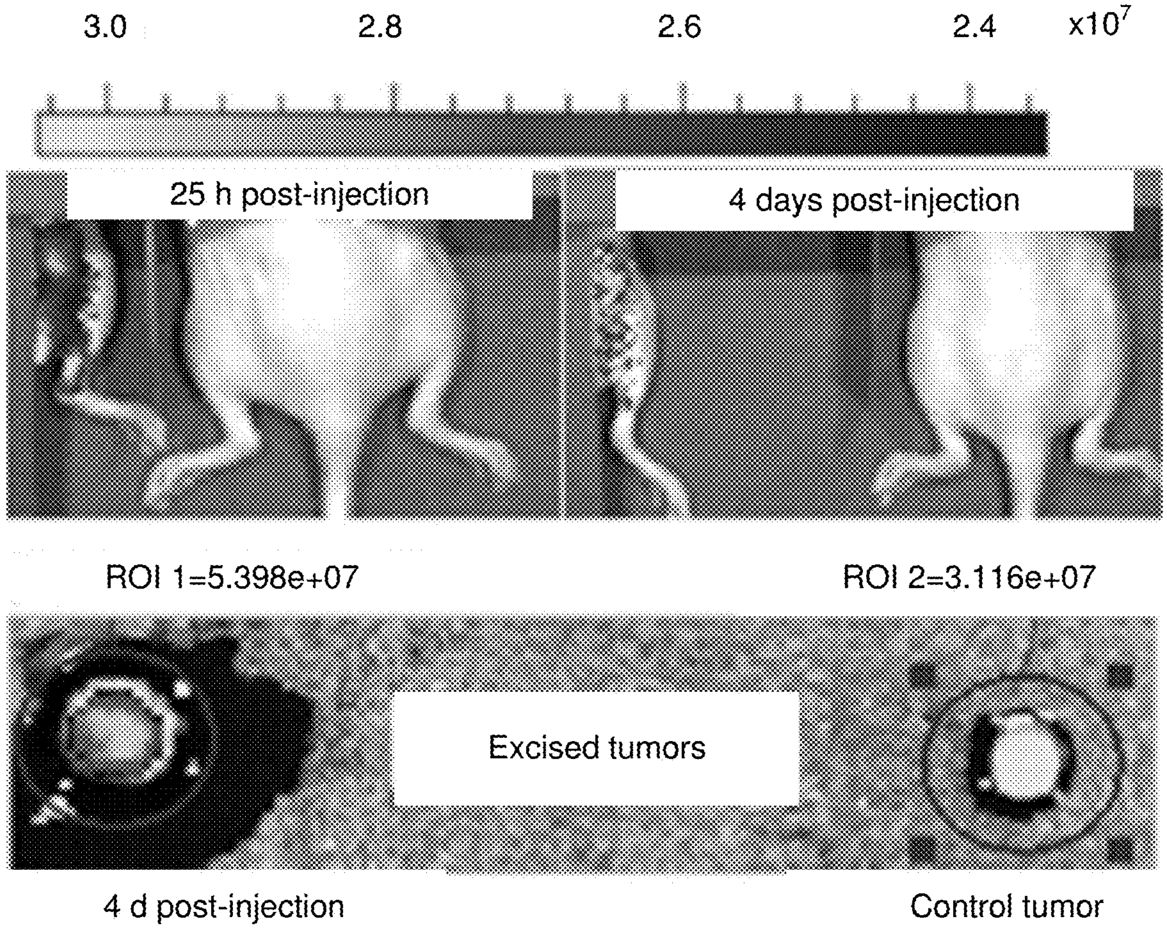
FIG. 9 shows images of NPs biodistribution in vivo (top) in the OvCA mouse model and excised tumors (bottom) from a NP-injected mouse (left) and a control PBS-injected mouse (right).

Finally, we evaluated the potential of RGDFFF (SEQ ID NO: 1)-Cy7 NPs (no drugs) to target solid tumors in a subcutaneous model of OvCA. The Cy7 labeled NPs, at the same dose as in half-life studies, were IV injected via tail vein into OVCAR-3-tumor bearing nude mice. The NPs biodistribution studies in vivo were performed using an IVIS small animal imaging system. Twenty-four hours post-injection, no fluorescence signal was detected in controls, but a strong NIR signal was observed at the tumor site in the NPs injected mice (FIG. 9, top left). Moreover, after four days, the intratumoral NIR signal remained strong, indicating prolonged retention of the NPs in the tumor (FIG. 9, top right). At this time point, the tumors were excised and examined ex vivo by NIR fluorescence. FIG. 9 (bottom) demonstrates the greater fluorescence in the tumor than in control, as established from the measured regions of interest (ROIs).

Figure 10:
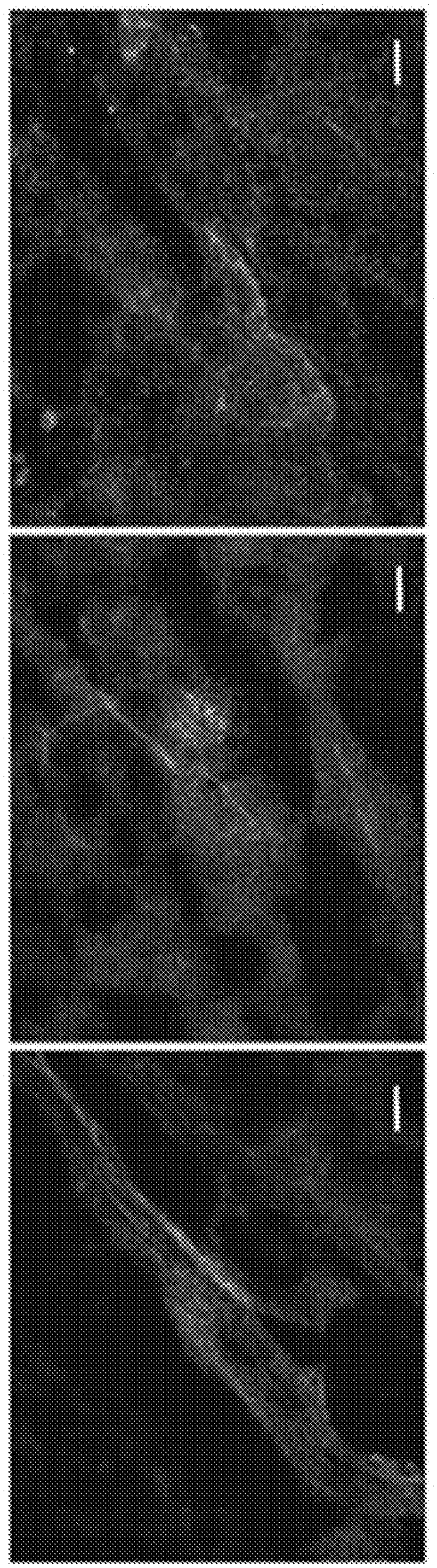
FIG. 10 are confocal images of frozen sections of OVCAR-3 tumors excised after 4 days from the mouse injected with RGDFFF (SEQ ID NO: 1)-Cy7 NPs. The CD31 staining of vascular endothelial cells appears in red, and RGDFFF (SEQ ID NO: 1)-Cy7 NPs are in green; the nuclei are stained with DAPI (blue). Scale bars represent 10 μm. The sections clearly show the association of the NPs with the blood vessels and tumor cells.

In addition, tumor cross-sections were imaged to investigate the intratumoral distribution of the RGDFFF (SEQ ID NO: 1)-Cy7 NPs. Frozen tumor sections were prepared using a cryostat. Standard immunostaining techniques were applied for CD31 (endothelial cells) and DAPI. Briefly, sections were blocked with donkey serum for 20 min at room temperature (RT), washed with PBS, and incubated with rat anti-mouse CD31 antibody for 45 min at RT. Slides were rinsed with PBS and incubated with secondary donkey anti-rat antibody labeled with Cy3 for 30 min, rinsed with PBS, and mounted in mounting medium with DAPI. The stained tumor sections were imaged using LSM 880 Airyscan Fast Live Cell confocal microscope using the appropriate filters and 63× magnification. The images are shown in FIG. 10. The vascular endothelial cells are shown in red, and the association of the RGDFFF (SEQ ID NO: 1)-Cy7 NPs (green) with tumor blood vessels is apparent. Notably, the NPs are also prominently combined with tumor cells (stained with DAPI) suggesting that the NPs effectively bind to tumor-associated vasculature and successfully extravasate into tumor interstitium. These results demonstrate that the RGDFFF (SEQ ID NO: 1)-coated NPs exhibit tumor-targeting capabilities and are suitable as drug delivery vehicles for OvCA therapy. The RGDFFF (SEQ ID NO: 1)-Cy7 NP biodistribution into organs was also investigated using NIRF. The RGDFFF (SEQ ID NO: 1)-Cy7 NPs were found in the liver, spleen, and lungs, but were not detected in the brain, which indicates that the NP did not cross the blood-brain barrier. Complete in vivo efficacy studies using the RGDFFF (SEQ ID NO: 1)-CA4 NP in OvCA tumor models are underway.

The uptake of RGDFFF (SEQ ID NO: 1)-Cy5.5 NP in patient-derived OvCA cells was tested. While commercially available cell lines have been used in pre-clinical research and have been extremely useful in advancing the understanding of cancer biology, they do not truly represent the characteristics of original tumors. In the present studies, the uptake of empty RGDFFF (SEQ ID NO: 1)-Cy5.5 NP (no drug) was examined in six PDCLs: four derived from patients with high-grade serous ovarian cancer (PT217, PT927, PT1264, PT1310) and two with serous endometrial cancer (PT1315, PT1332).

Figure 11:
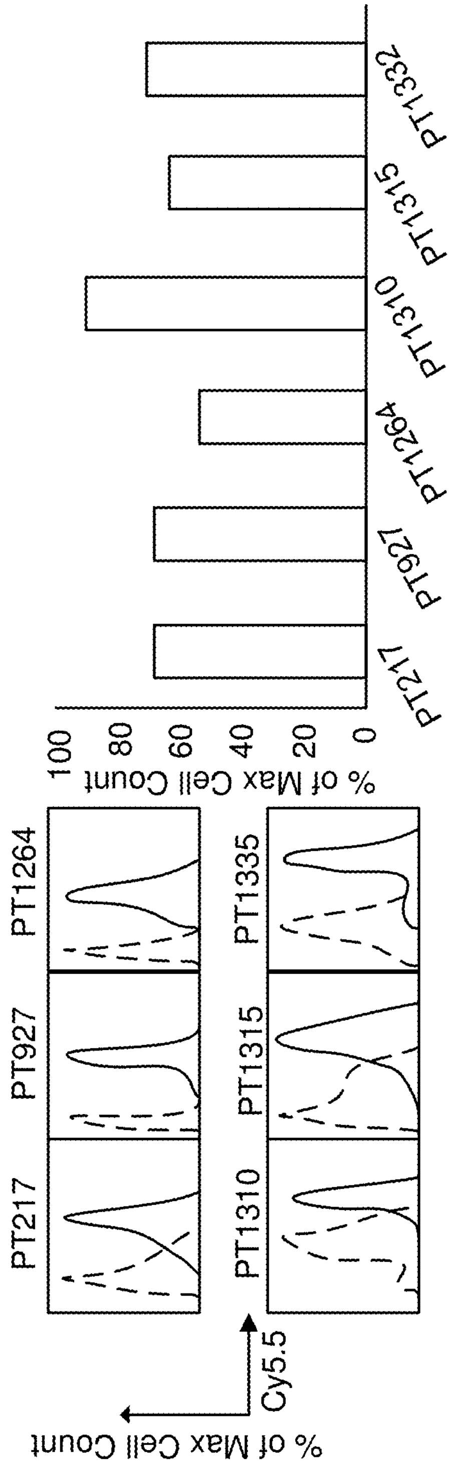
FIG. 11 depicts the results of flow Cytometry analysis of RGDFFF (SEQ ID NO: 1)-Cy5.5 NP uptake by PDCLs. Dash lines shows blank (non-treated cell), and solid lines shows cells incubated with RGDFFF (SEQ ID NO: 1)-Cy5.5 NPs. The X-axis is the Cy5.5 intensity, and Y-axis is the number of cells. The table characterizes the percent of NP-positive cells from three trials.

Cells were incubated with the NP for 15 min, washed with PBS, and collected in suspension. The fluorescence was measured using flow cytometry, and the results are presented in FIG. 11. The analysis of RGDFFF (SEQ ID NO: 1)-Cy5.5 NP uptake shows more than 50% positivity for all six PDCLs [range 53-91%].

Synthesis of PLGA-CA4 hybrid. First, 200 mg (0.05 mmol) of 1-5 kDa PLGA polymer was dissolved in 2 mL of anhydrous dichloromethane, followed by addition of 41 mg (0.2 mmol) of DCC and 24 mg (0.2 mmol) of DMAP. Next, 16 mg (0.05 mmol) of CA4 was dissolved in 2 mL of anhydrous dichloromethane and added dropwise to the PLGA solution. The reaction mixture was stirred overnight at room temperature. $^{1}$H NMR was used to monitor the progress of the coupling reaction between CA4 and PLGA. Once the reaction was complete, the crude product was dried using rotary evaporator and dissolved in a small amount of acetonitrile. Next, the solution was added dropwise to cold methanol and kept at −20° C. overnight. After that, the product was centrifuged and dissolved in acetonitrile. Last three steps were repeated 3 times to obtain a pure product. The yield of the reaction was determined to be 32%.

Synthesis of RGDFFF-PLGA-CA4 NPs. PLGA-CA4 (5 mg, 0.0012 mmol) was dissolved in 2 mL of acetonitrile and added dropwise using a syringe pump (0.2 mL/min flow) into RGDFFF (SEQ ID NO: 1) peptide (1.5 mg, 0.0019 mmol) 6 mL solution in nanpure water at 37° C. The solution was stirred overnight to allow the self-assembly of RGDFFF (SEQ ID NO: 1)-CA4 NPs. The NPs were concentrated using Vivaspin centrifugal concentrator (100 k MWCO) and washed 3 times with nanopure water.

Comparative Example 1—Temperature

Figure 12:
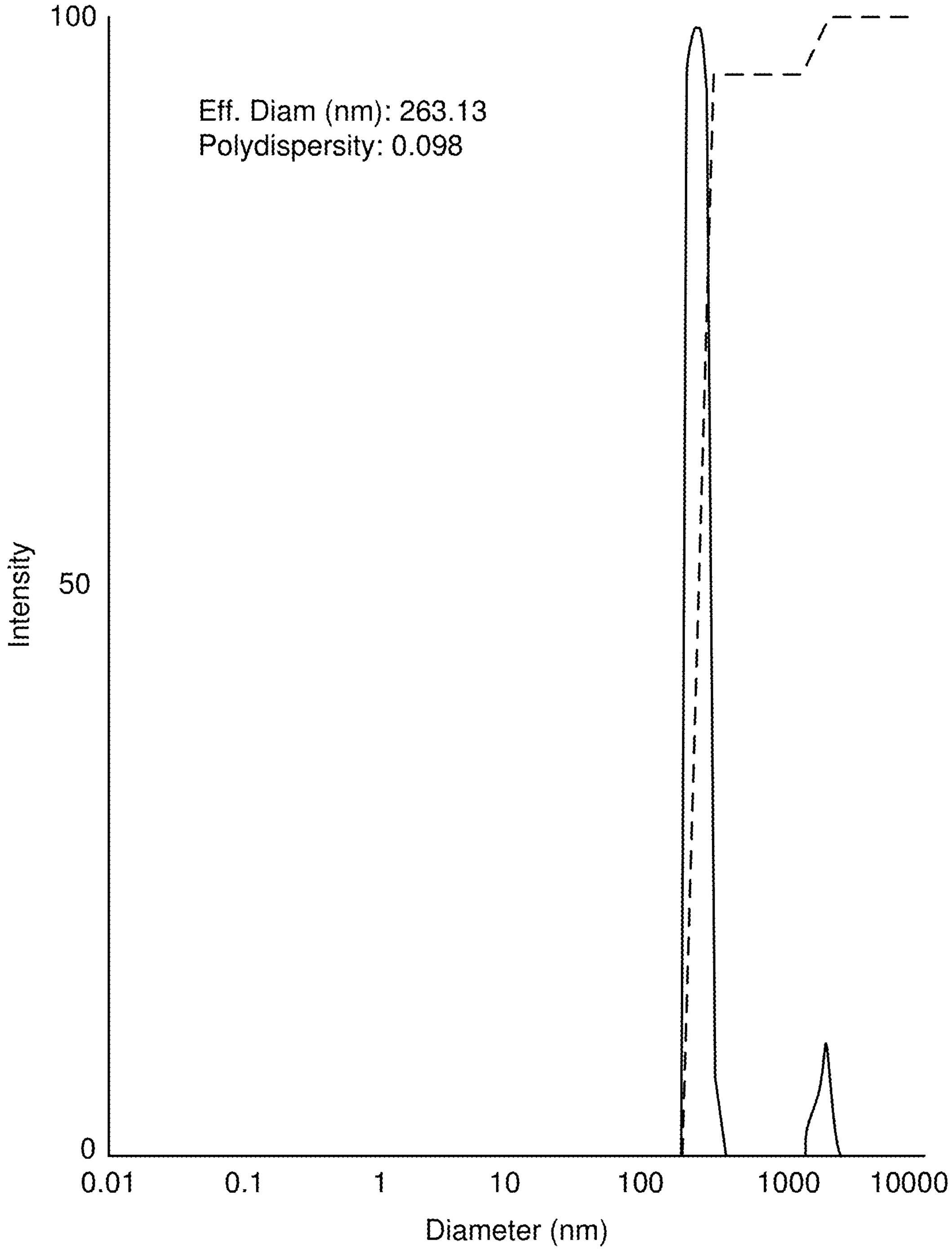
FIG. 12 is a DLS plot showing increased NP size due to the process being conducted at an elevated temperature.

TPP-KFF peptide coated PLGA nanoparticles were synthesized according to previously described protocol with the exception that the temperature of the process was 37° C. instead of 22° C. More pronounced cloudiness is associated with larger nanoparticle size of 263 nm was observed. FIG. 12 shows the particle size is greater than 100 nm.

Comparative Example 2—Stirring Rate

Figure 13A:
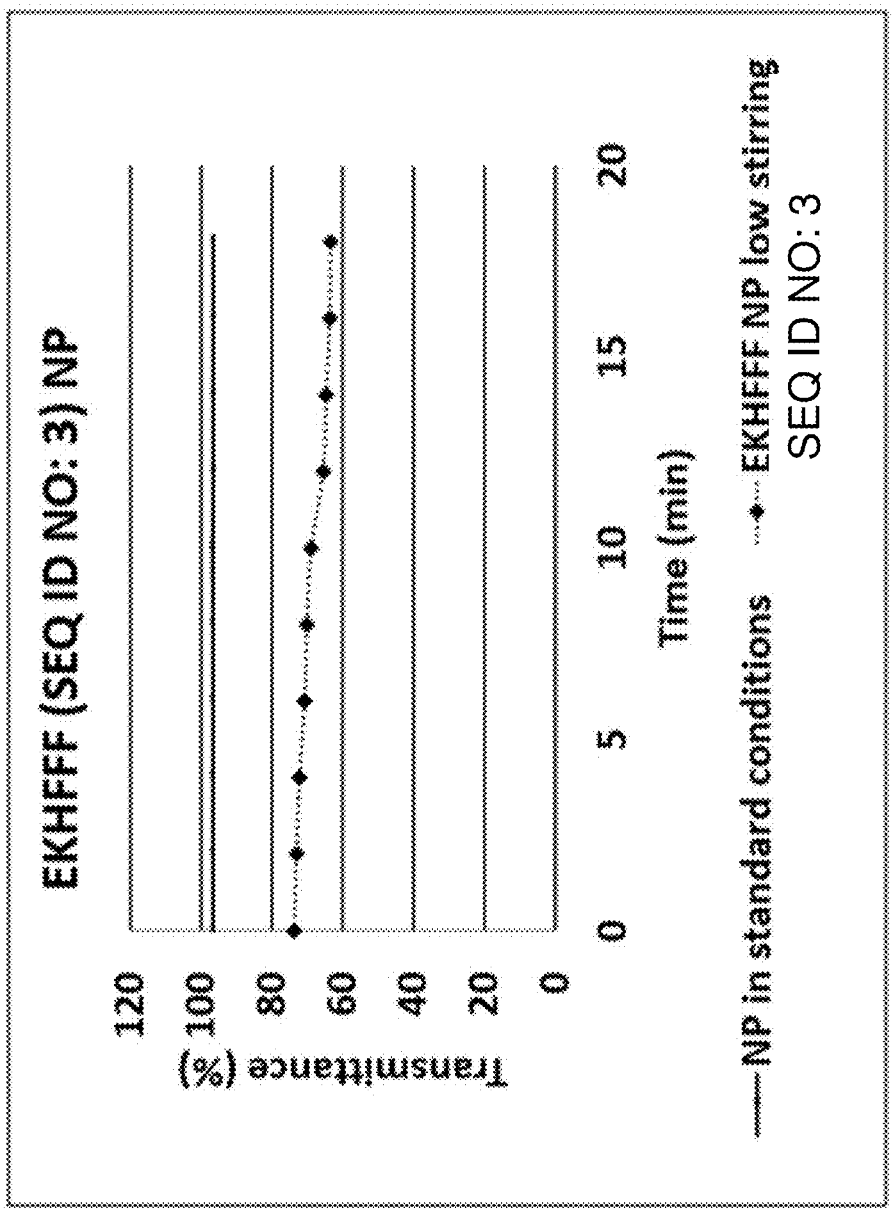
FIG. 13A is a graph of percent transmittance of a comparative example showing increase in turbidity due to the process being conducted at a reduced up to 600 rpm stir rate.
Figure 13B:
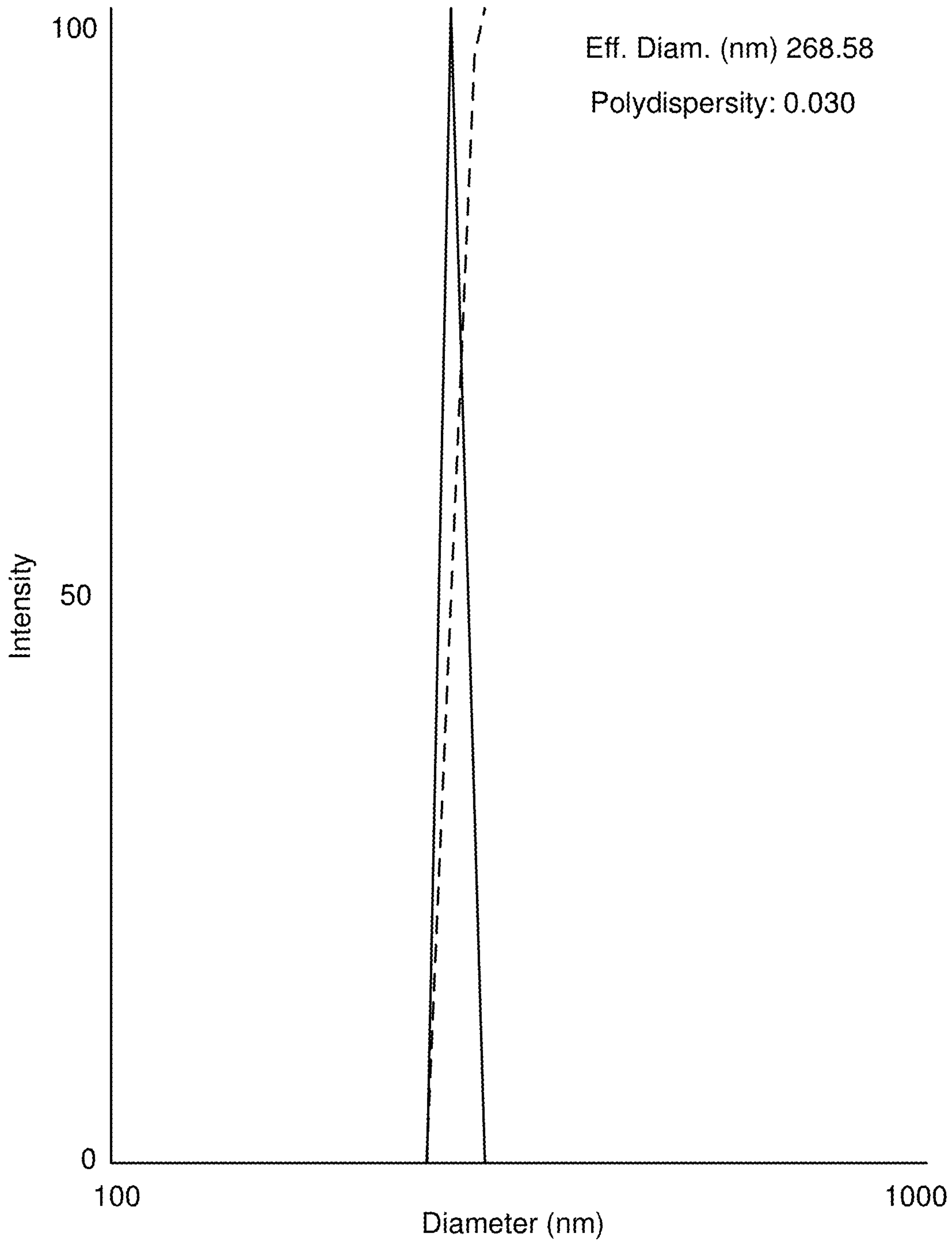
FIG. 13B is a DLS plot showing increased NP size due to the process being conducted at a reduced up to 600 rpm stir rate.

EKHFFF (SEQ ID NO: 3) peptide coated PLGA nanoparticles were synthesized according to previously described protocol with the exception that the stirring rate of the peptide solution was adjusted to 600 rpm. Results are presented in FIG. 13A. More pronounced cloudiness is associated with larger nanoparticle size of 268 nm. FIG. 13B shows the particle size is greater than 100 nm.

Comparative Example 3—Peptide Concentration

Figure 14A:
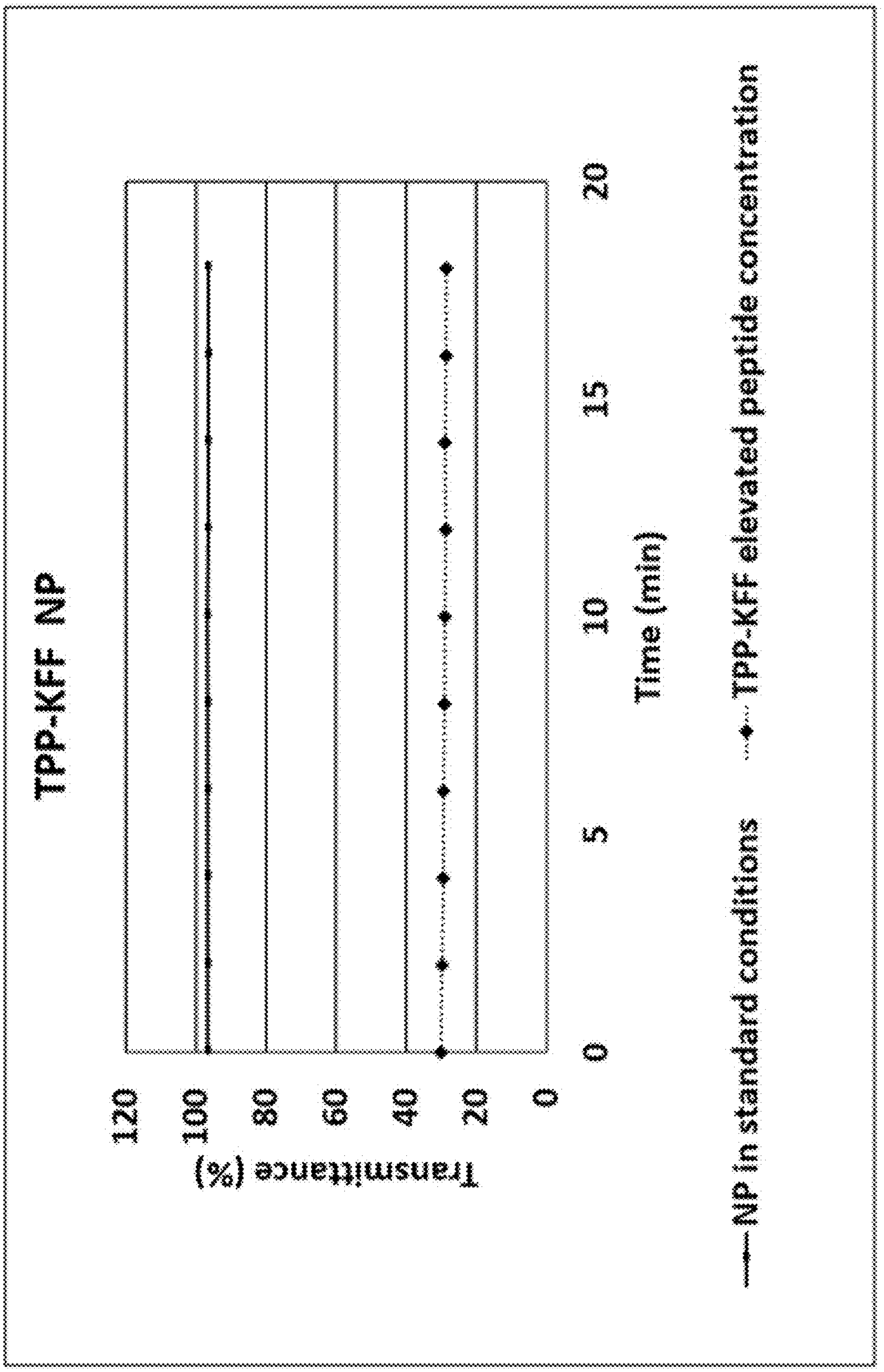
FIG. 14A is a graph of percent transmittance of a comparative example showing increase in turbidity due to the process being conducted at an elevated peptide concentration.
Figure 14B:
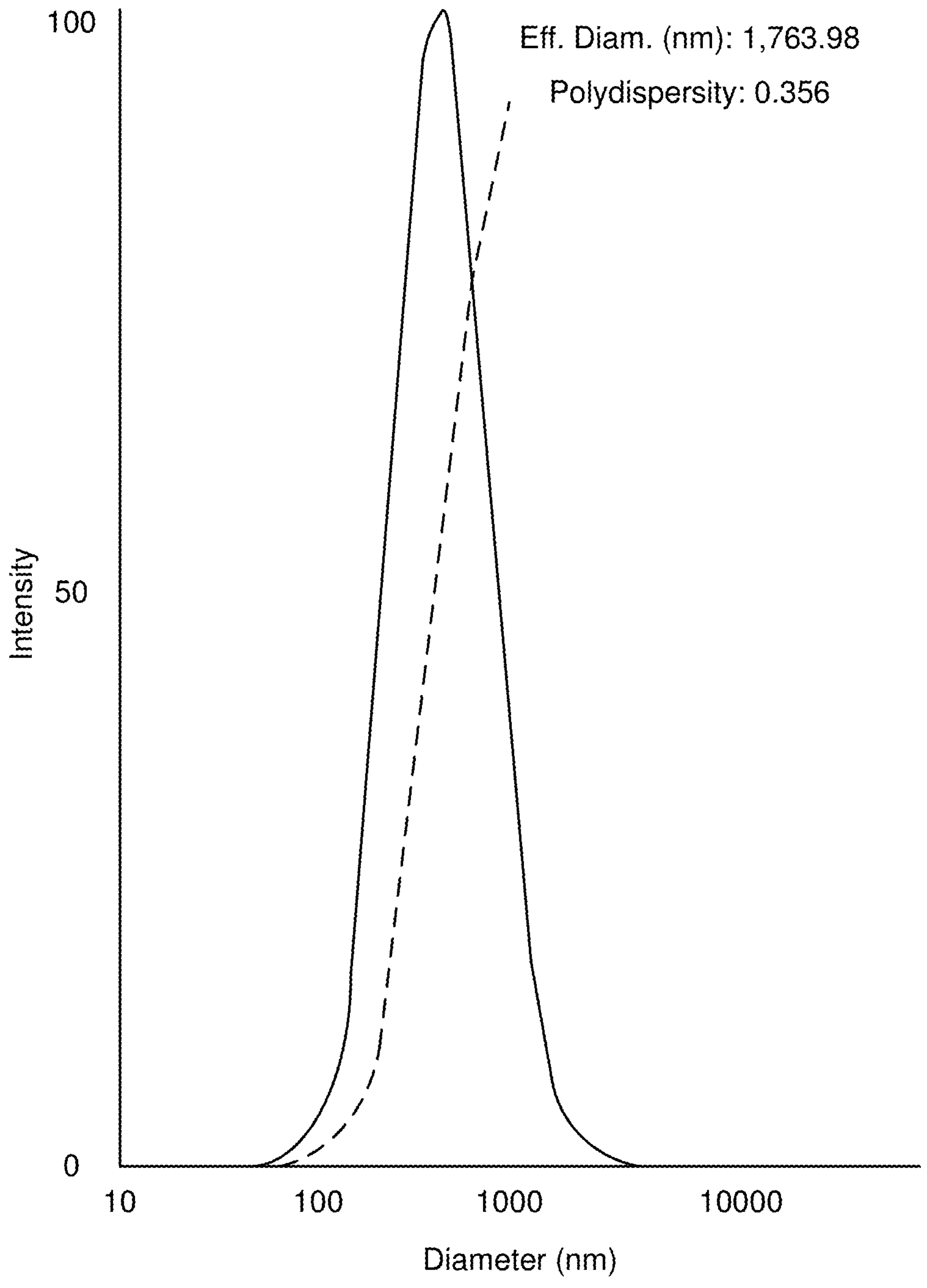
FIG. 14B is a DLS plot showing increased NP size due to the process being conducted at an elevated peptide concentration.

TPP-KFF peptide coated PLGA nanoparticles were synthesized according to previously described protocol with the exception that the peptide concentration was elevated (i.e. 0.4 mg per mL). Cloudiness was observed within 20-30 min after addiction was completed. FIG. 14A shows increased turbidity. In the turbidity experiment, transmittance (the quantity of light that passes through the solution) of a nanoparticle-peptide-coated solution was measured using the standard method of synthesis (solid line) and under altered conditions (dashed line). The stable nanoparticle solution is opalescent and transparent, exhibiting a high percentage of transmittance. However, when nanoparticles have a tendency to aggregate, the transmittance of the solution decreases significantly, resulting in a lower level of transparency in the solution. More pronounced cloudiness is associated with larger particle size of 1.764 m (FIG. 14B).

Comparative Example 4—PLGA Concentration

Figure 15:
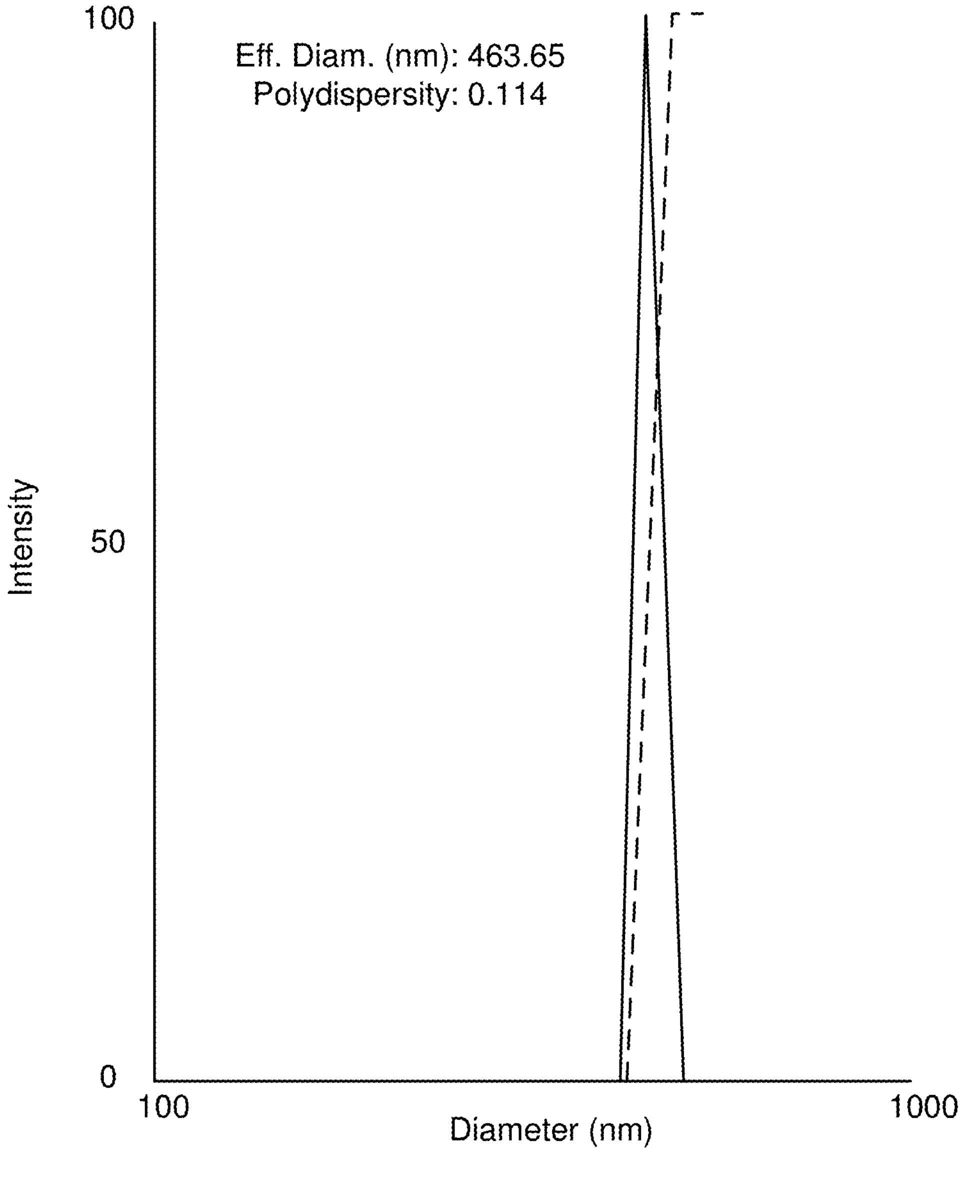
FIG. 15 is a DLS plot showing increased NP size due to the process being conducted at an elevated PLGA concentration.

EKHFFF (SEQ ID NO: 3) peptide coated PLGA nanoparticles were synthesized according to previously described protocol with the exception that the PLGA concentration was elevated (i.e. 10 mg per 1.5 mL). More pronounced cloudiness is associated with larger nanoparticle size of 464 nm. See FIG. 15.

Comparative Example 5—Effects of Sonication

Figure 16A:
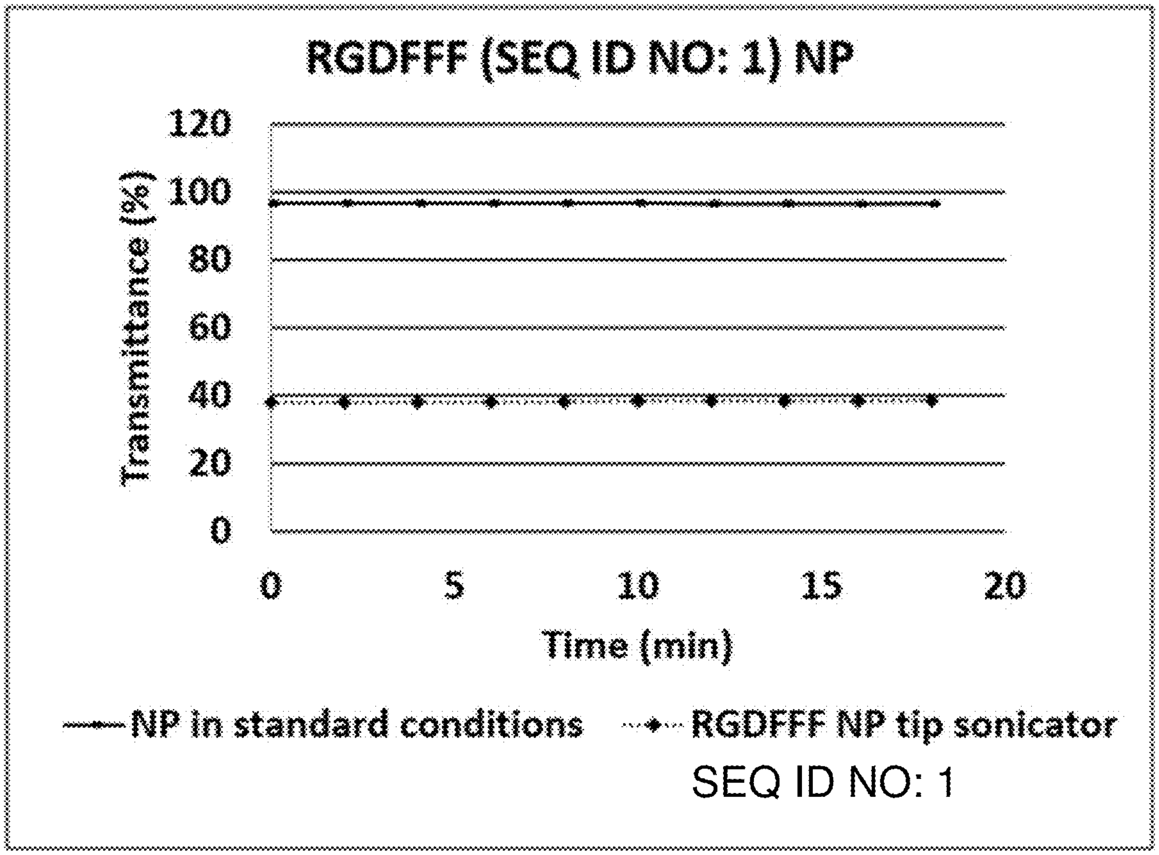
FIG. 16A is a graph of percent transmittance of a comparative example showing increase in turbidity due to the process being conducted with sonication.
Figure 16B:
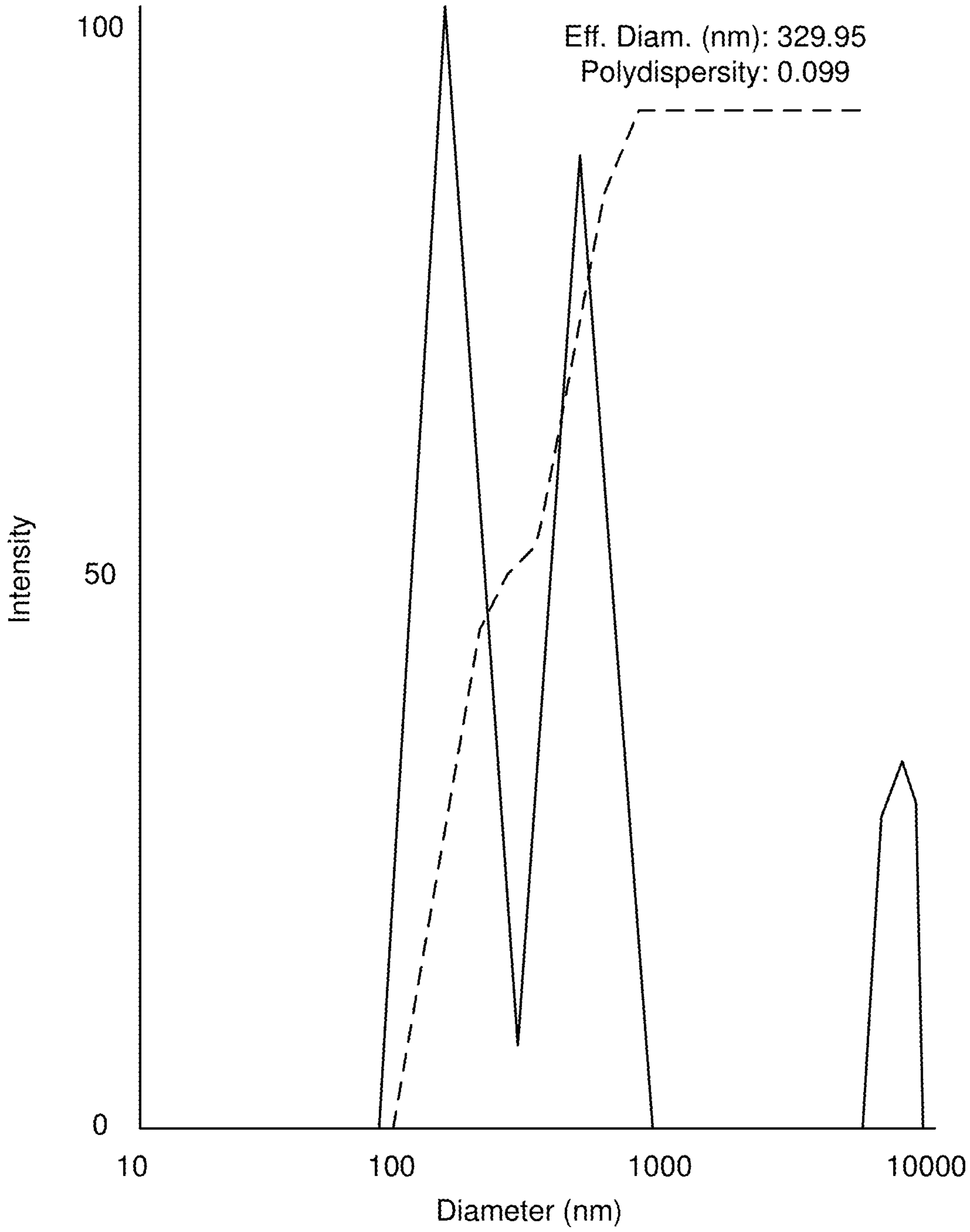
FIG. 16B is a DLS plot showing increased NP size due to the process being conducted with sonication.

Traditional methods of polymeric nanoparticle synthesis require, for example ultrasonication with tip sonicator. Sonication disperses aggregated nanoparticles for better water dispersion. However, the RGDFFF (SEQ ID NO: 1) peptide coated PLGA nanoparticles precipitated out after sonication for 3 min 1:1 pulse and 30% amplitude. When this was attempted with PLGA particles coated with SEQ ID NO: 1, opalescence indicates presence of the stable nanoparticles dispersed in water while cloudiness indicates aggregation and precipitation of the nanoparticles. Transmittance of a nanoparticle-peptide-coated solution was measured using the standard method of synthesis (solid line) and under altered conditions (dashed line). The stable nanoparticle solution is opalescent and transparent, exhibiting a high percentage of transmittance. However, when nanoparticles have a tendency to aggregate, the transmittance of the solution decreases significantly, resulting in a lower level of transparency in the solution. More pronounced cloudiness is associated with larger nanoparticle size of 329 nm. See FIG. 16A and FIG. 16B. The disclosed method is therefore conducted without sonication.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

SEQUENCE LISTING

```
Sequence total quantity: 3
SEQ ID NO: 1          moltype = AA  length = 6
FEATURE               Location/Qualifiers
source                1..6
```

-continued

```
                         mol_type = protein
                         organism = Synthetic construct
SEQUENCE: 1
RGDFFF                                                  6

SEQ ID NO: 2             moltype = AA  length = 6
FEATURE                  Location/Qualifiers
source                   1..6
                         mol_type = protein
                         organism = Synthetic construct
SEQUENCE: 2
NGRFFF                                                  6

SEQ ID NO: 3             moltype = AA  length = 6
FEATURE                  Location/Qualifiers
source                   1..6
                         mol_type = protein
                         organism = Synthetic construct
SEQUENCE: 3
EKHFFF                                                  6
```

What is claimed is:

1. A method for synthesizing a nanoparticle, the method comprising sequential steps of:

diluting a hexapeptide in nanopure water to a concentration from 0.1 mg per mL to 0.25 mg per mL, wherein the hexapeptide is selected from a group consisting of EKHFFF, NGRFFF and RGDFFF thereby producing a diluted hexapeptide solution;

adding a solution of PLGA in acetonitrile dropwise at a rate of between 0.05 mL per min and 0.5 mL per min to the diluted hexapeptide solution while maintaining the diluted hexapeptide solution at a temperature of 37±3 C for EKHFFF, NGRFFF and RGDFFF, wherein a total mass of the hexapeptide and a total mass of the PLGA are present in a mass ratio of 1:5 for EKHFFF or NGRFFF or a mass ratio of 1.5:5 for RGDFFF;

stirring for at least 10 hours at a temperature between 20° C. and 25° C. to produce a raw solution; and dialyzing the raw solution to remove contaminates, thereby producing nanoparticles.

2. The method as recited in claim 1, wherein the solution of PLGA in acetonitrile has a concentration of 5 mg per 3 mL.

3. The method as recited in claim 1, wherein the hexapeptide is EKHFFF and the concentration is 0.17 mg per mL.

4. The method as recited in claim 1, wherein the hexapeptide is NGRFFF and the concentration is 0.17 mg per mL.

5. The method as recited in claim 1, wherein the hexapeptide is RGDFFF and the concentration is 0.25 mg per mL.

6. The method as recited in claim 1, wherein the temperature between 20° C. and 25° C. is 22° C.

7. The method as recited in claim 1, wherein the stirring for at least 10 hours stirred at a rate of 200 rpm.

8. The method as recited in claim 7, wherein the adding the solution of PLGA in acetonitrile dropwise is simultaneously accompanied by stirring the diluted hexapeptide solution at a rate of 700-1000 rpm.

9. The method as recited in claim 8, wherein the dialyzing the raw solution is performed with a 3.5 kDa membrane in nanopure water.

10. The method as recited in claim 1, wherein the nanoparticles have a diameter of ≤100 nm.

* * * * *